United States Patent
Nakayama et al.

(10) Patent No.: US 10,219,756 B2
(45) Date of Patent: *Mar. 5, 2019

(54) RADIOGRAPHY DEVICE, RADIOGRAPHY METHOD, AND RADIOGRAPHY PROGRAM

(71) Applicant: FUJIFILM CORPORATION, Minato-ku, Tokyo (JP)

(72) Inventors: Hiroki Nakayama, Kanagawa (JP); Takeyasu Kobayashi, Kanagawa (JP); Tomoki Inoue, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 365 days.

This patent is subject to a terminal disclaimer.

(21) Appl. No.: 15/150,438

(22) Filed: May 10, 2016

(65) Prior Publication Data

US 2016/0249868 A1 Sep. 1, 2016

Related U.S. Application Data

(63) Continuation of application No. PCT/JP2014/078525, filed on Oct. 27, 2014.

(30) Foreign Application Priority Data

Nov. 11, 2013 (JP) .................................. 2013-233154

(51) Int. Cl.
*A61B 6/00* (2006.01)
*A61B 6/02* (2006.01)
*A61B 6/04* (2006.01)

(52) U.S. Cl.
CPC ............ *A61B 6/025* (2013.01); *A61B 6/0414* (2013.01); *A61B 6/405* (2013.01); *A61B 6/4085* (2013.01);
(Continued)

(58) Field of Classification Search
CPC ....... A61B 6/025; A61B 6/502; A61B 6/0414; A61B 6/469; A61B 6/50; A61B 6/5205; A61B 6/5223; A61B 6/54; A61B 6/541
See application file for complete search history.

(56) References Cited

U.S. PATENT DOCUMENTS 7,831,296 B2 11/2010 Defreitas et al.
2006/0269040 A1* 11/2006 Mertelmeier .......... A61B 6/466
378/37

(Continued)

*Primary Examiner* — Chih-Cheng Kao
(74) *Attorney, Agent, or Firm* — Solaris Intellectual Property Group, PLLC

(57) ABSTRACT

Provided are a radiography device, a radiography method, and a radiography program which can obtain an accurate radiographic image while reducing a burden on a subject. A radiography device control unit determines imaging conditions including at least one of resolution or an incident angle range, on the basis of a radiographic image captured before tomosynthesis imaging, and performs tomosynthesis imaging. Specifically, the radiography device control unit controls tomosynthesis imaging (120) such that tomosynthesis imaging is performed under first conditions (108) of low resolution and a narrow incident angle range in a case in which a mutation site suspected as a lesion is not detected and tomosynthesis imaging is performed under second conditions (112, 116, and 118) which are different from the first conditions in at least one of the resolution or the incident angle range in a case in which the mutation site suspected as a lesion is detected.

15 Claims, 10 Drawing Sheets

(52) U.S. Cl.
CPC ............ *A61B 6/4233* (2013.01); *A61B 6/469* (2013.01); *A61B 6/502* (2013.01); *A61B 6/5205* (2013.01); *A61B 6/5217* (2013.01); *A61B 6/542* (2013.01); *A61B 6/544* (2013.01); *A61B 6/545* (2013.01)

(56) References Cited

U.S. PATENT DOCUMENTS

| | | | | |
|---|---|---|---|---|
| 2007/0036265 | A1* | 2/2007 | Jing | A61B 6/025 378/37 |
| 2014/0226783 | A1* | 8/2014 | Ning | A61B 6/032 378/5 |
| 2016/0256119 | A1* | 9/2016 | Nakayama | A61B 6/025 |

* cited by examiner

FIG. 7A

| | RESOLUTION | SWING ANGLE |
|---|---|---|
| NOT DETECTED | LOW RESOLUTION (BINNING PROCESS) | NARROW INCIDENT ANGLE RANGE |
| DETECTION OF CALCIFICATION | HIGH RESOLUTION | NARROW INCIDENT ANGLE RANGE |
| DETECTION OF TUMOR MASS | LOW RESOLUTION | WIDE INCIDENT ANGLE RANGE |
| DETECTION OF CALCIFICATION AND TUMOR MASS | HIGH RESOLUTION | WIDE INCIDENT ANGLE RANGE |

FIG. 7B

| | RESOLUTION | SWING ANGLE |
|---|---|---|
| NOT DETECTED | LOW RESOLUTION (BINNING PROCESS) | NARROW INCIDENT ANGLE RANGE |
| DETECTION OF CALCIFICATION | HIGH RESOLUTION | NARROW INCIDENT ANGLE RANGE |
| DETECTION OF TUMOR MASS | HIGH RESOLUTION | WIDE INCIDENT ANGLE RANGE |
| DETECTION OF CALCIFICATION AND TUMOR MASS | HIGH RESOLUTION | WIDE INCIDENT ANGLE RANGE |

FIG. 7C

| | RESOLUTION | SWING ANGLE |
|---|---|---|
| NOT DETECTED | LOW RESOLUTION (BINNING PROCESS) | NARROW INCIDENT ANGLE RANGE |
| DETECTION OF MUTATION SITE | HIGH RESOLUTION | WIDE INCIDENT ANGLE RANGE |

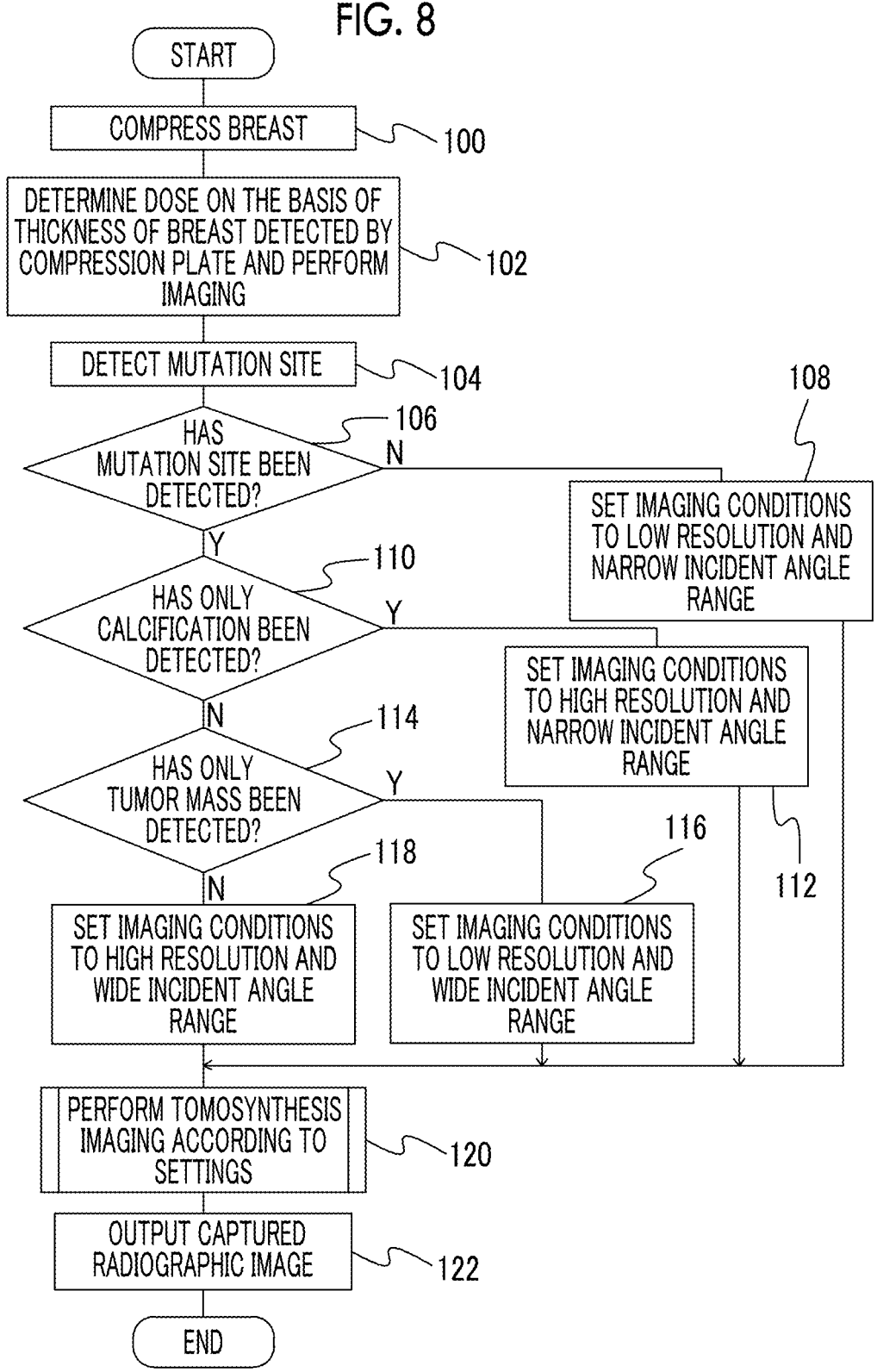

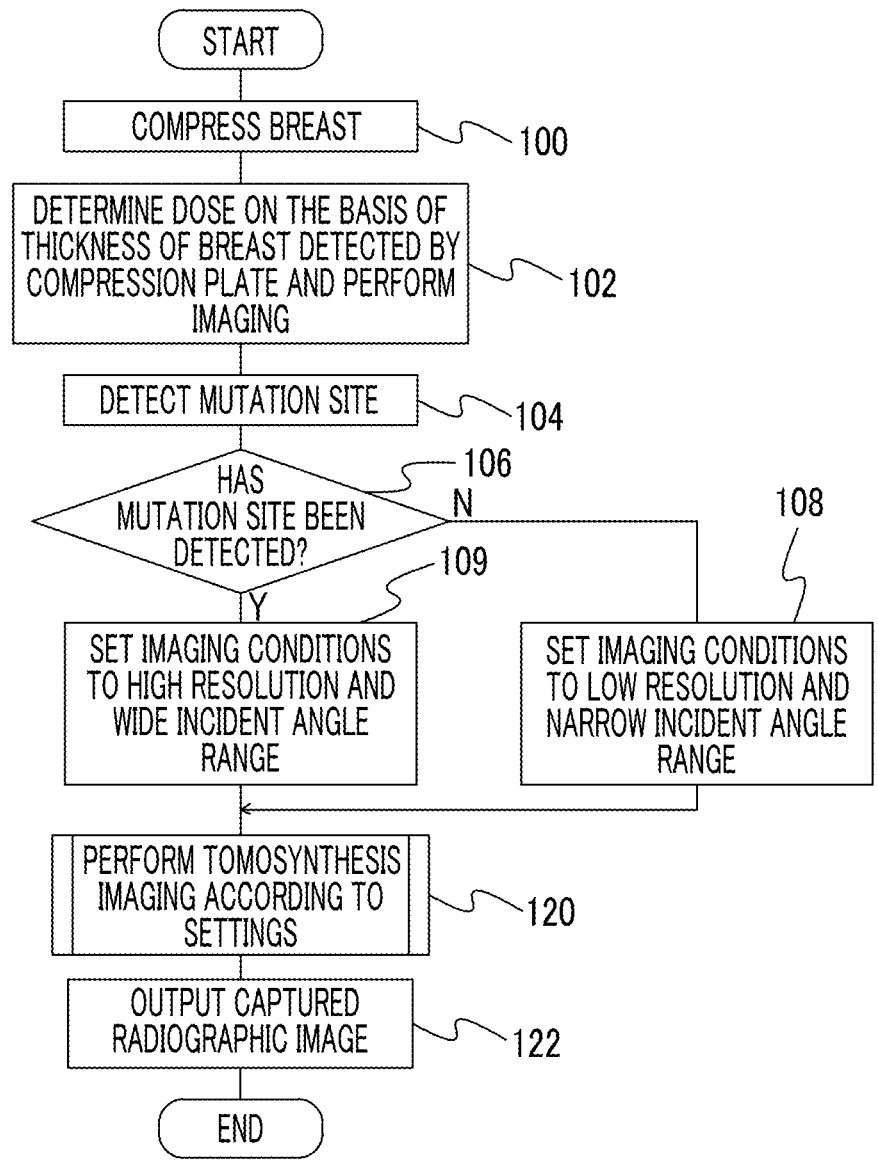

RADIOGRAPHY DEVICE, RADIOGRAPHY METHOD, AND RADIOGRAPHY PROGRAM

CROSS-REFERENCE TO RELATED APPLICATIONS

This application is a continuation application of International Application No. PCT/JP2014/078525, filed on Oct. 27, 2014, which is incorporated herein by reference in its entirety. Further, this application claims priority from Japanese Patent Application No. 2013-233154, filed on Nov. 11, 2013, the disclosure of which is incorporated by reference herein in its entirety.

BACKGROUND

1. Field of the Invention

The present invention relates to a radiography device, a radiography method, and a radiography program storage medium.

2. Description of the Related Art

A radiography device is known which captures radiographic images for medical diagnosis. An example of this type of radiography device is a mammography device which captures an image of the breast of a subject for the early detection of breast cancer. In addition, in mammography, a tomosynthesis imaging technique is known which irradiates the breast of the subject with radiation at different angles to capture images of the breast. The tomosynthesis imaging technique reconstructs a plurality of radiographic images, which are captured by irradiating the subject with radiation at different incident angles with respect to a radiation detection surface in a predetermined range, to generate tomographic images.

For example, U.S. Pat. No. 7,831,296B discloses a technique which performs mammography and tomosynthesis imaging using one process of compressing the breast.

In the technique disclosed in U.S. Pat. No. 7,831,296B, mammography and tomosynthesis imaging are performed by one process of compressing the breast. However, in the technique, imaging conditions are determined before imaging, regardless of, for example, whether a lesion is present or the type of lesion, and imaging is performed. Therefore, the technique needs to be improved in order to obtain an accurate radiographic image.

SUMMARY

The invention has been made in view of the above-mentioned problems and an object of the invention is to provide a radiography device, a radiography method, and a radiography program storage medium, which can obtain an accurate radiographic image while reducing a burden on a subject.

According to a first aspect of the invention, there is provided a radiography device that can perform tomosynthesis imaging. The radiography device comprises: a radiation emitting unit that irradiates a subject with radiation at a plurality of different incident angles; a radiographic image generation unit that receives the radiation which has been emitted from the radiation emitting unit and passed through the subject and can generate radiographic images of the subject with different resolutions; a part-of-interest detection unit that detects a mutation site suspected as a lesion from the radiographic image of the subject which is generated by the radiographic image generation unit with the radiation emitted from the radiation emitting unit to the subject at a predetermined incident angle before the tomosynthesis imaging; and a radiography device control unit that performs control such that a first tomosynthesis imaging process in which the tomosynthesis imaging is performed in a first incident angle range and the radiographic image generation unit generates a plurality of projection images of the subject at a first resolution is performed in a case in which the part-of-interest detection unit does not detect the mutation site and a second tomosynthesis imaging process is performed at least in a second incident angle range wider than the first incident angle range or at a second resolution higher than the first resolution in a case in which the part-of-interest detection unit detects the mutation site.

In the radiography device according to the first aspect, the radiation emitting unit irradiates the subject with radiation at a plurality of different incident angles. In addition, the radiographic image generation unit receives the radiation which has been emitted from the radiation emitting unit and passed through the subject and can generate the radiographic images of the subject with different resolutions.

The part-of-interest detection unit detects the mutation site suspected as a lesion from the radiographic image of the subject which is generated by the radiographic image generation unit with the radiation emitted from the radiation emitting unit to the subject at a predetermined incident angle before the tomosynthesis imaging.

Then, the radiography device control unit performs control such that the first tomosynthesis imaging process in which the tomosynthesis imaging is performed in the first incident angle range and the radiographic image generation unit generates a plurality of projection images of the subject at the first resolution is performed in a case in which the part-of-interest detection unit does not detect the mutation site and the second tomosynthesis imaging process is performed at least in the second incident angle range wider than the first incident angle range or at the second resolution higher than the first resolution in a case in which the part-of-interest detection unit detects the mutation site.

That is, the time required for tomosynthesis imaging depends on imaging conditions, such as resolution and an incident angle range. Therefore, the imaging conditions vary, depending on whether a mutation site is present in the radiographic image captured before tomosynthesis imaging, and tomosynthesis imaging is performed. As a result, it is possible to obtain an accurate radiographic image while reducing a burden on the subject.

For example, in a case in which the part-of-interest detection unit detects only the mutation site with the first size in the predetermined range, the radiography device control unit may perform control such that the second tomosynthesis imaging process is performed at the second resolution and in the first incident angle range. In addition, the first size is in a predetermined range.

In a case in which the part-of-interest detection unit detects both the mutation site with the first size in the predetermined range and the mutation site with a size greater than the first size, the radiography device control unit may perform control such that the second tomosynthesis imaging process is performed at the second resolution and in the second incident angle range.

In a case in which the part-of-interest detection unit detects only the mutation site with a size greater than the first size in the predetermined range, the radiography device control unit may perform control such that the second tomosynthesis imaging process is performed at the first resolution and in the second incident angle range.

In a case in which the part-of-interest detection unit detects only the mutation site with a size greater than the first size in the predetermined range, the radiography device control unit may perform control such that the second tomosynthesis imaging process is performed at the second resolution and in the second incident angle range.

The mutation site with a size greater than the first size may be a mutation site suspected as a tumor mass. In addition, the mutation site with the first size may be a mutation site suspected as a calcification.

According to a second aspect of the invention, there is provided a radiography method that is performed in a radiography device which can perform tomosynthesis imaging and comprises a radiation emitting unit that irradiates a subject with radiation at a plurality of different incident angles and a radiographic image generation unit that receives the radiation which has been emitted from the radiation emitting unit and passed through the subject and can generate radiographic images of the subject with different resolutions. The radiography method comprises: allowing the radiation emitting unit to irradiate the subject with the radiation at a predetermined incident angle, allowing the radiographic image generation unit to generate a radiographic image of the subject, and detecting a mutation site suspected as a lesion from the radiographic image, before the tomosynthesis imaging; performing a first tomosynthesis imaging process in which the tomosynthesis imaging is performed in a first incident angle range and the radiographic image generation unit generates a plurality of projection images of the subject at a first resolution in a case in which the mutation site is not detected; and performing a second tomosynthesis imaging process at least in a second incident angle range wider than the first incident angle range or at a second resolution higher than the first resolution in a case in which the mutation site is detected.

In the radiography method according to the second aspect, the radiographic image is generated by the radiation emitting unit and the radiography image generation unit. First, before the tomosynthesis imaging, the radiation emitting unit irradiates the subject with the radiation at a predetermined incident angle, the radiographic image generation unit generates the radiographic image of the subject, and a mutation site suspected as a lesion is detected from the generated radiographic image.

Then, in a case in which the mutation site is not detected, the first tomosynthesis imaging process in which the tomosynthesis imaging is performed in the first incident angle range and the radiographic image generation unit generates a plurality of projection images of the subject at the first resolution is performed. In a case in which the mutation site is detected, the second tomosynthesis imaging process is performed at least in a second incident angle range wider than the first incident angle range or at a second resolution higher than the first resolution.

That is, the time required for tomosynthesis imaging depends on imaging conditions, such as resolution and an incident angle range. Therefore, the imaging conditions vary, depending on whether a mutation site is present in the radiographic image captured before tomosynthesis imaging, and tomosynthesis imaging is performed. As a result, it is possible to obtain an accurate radiographic image while reducing a burden on the subject.

For example, during imaging, in a case in which only the mutation site with a first size in a predetermined range is detected, the second tomosynthesis imaging process may be performed at the second resolution and in the first incident angle range. In addition, the first size is in a predetermined range.

During imaging, in a case in which both the mutation site with the first size in the predetermined range and the mutation site with a size greater than the first size are detected, the second tomosynthesis imaging process may be performed at the second resolution and in the second incident angle range.

During imaging, in a case in which only the mutation site with a size greater than the first size in the predetermined range is detected, the second tomosynthesis imaging process may be performed at the first resolution and in the second incident angle range.

During imaging, in the tomosynthesis imaging, in a case in which only the mutation site with a size greater than the first size in the predetermined range is detected, the second tomosynthesis imaging process may be performed at the second resolution and in the second incident angle range.

The mutation site with a size greater than the first size may be a mutation site suspected as a tumor mass. In addition, the mutation site with the first size may be a mutation site suspected as a calcification.

According to a third aspect of the invention, there is provided a radiography program that causes a computer to function as the radiography device control unit of the above-mentioned radiography device.

According to a fourth aspect of the invention, there is provided a non-transitory storage medium storing a program that causes a computer to execute radiography processing, the radiography processing including: irradiating, by a radiation emitting unit of a radiography device, a subject with radiation at a predetermined incident angle; generating, by a radiographic image generation unit of the radiography device, a radiographic image of the subject, and detecting a mutation site suspected as a lesion from the radiographic image; performing a first tomosynthesis imaging process in which a tomosynthesis imaging is performed in a first incident angle range and the radiographic image generation unit generates plural projection images of the subject at a first resolution in a case in which the mutation site is not detected; and performing a second tomosynthesis imaging process at least in a second incident angle range wider than the first incident angle range or at a second resolution higher than the first resolution in a case in which the mutation site is detected.

According to the above-mentioned aspects of the invention, it is possible to provide a radiography device, a radiography method, a radiography program, and a program storage medium which can obtain an accurate radiographic image while reducing a burden on a subject.

BRIEF DESCRIPTION OF THE DRAWINGS

FIG. 7A is a diagram illustrating a first example of the imaging conditions of the radiography device according to the embodiment.

FIG. 7B is a diagram illustrating a second example of the imaging conditions.

FIG. 7C is a diagram illustrating a third example of the imaging conditions.

FIG. 8 is a flowchart illustrating an example of the flow of a first example of a process performed by a radiography device control unit in the radiography system according to this embodiment.

FIG. 10 is a flowchart illustrating an example of the flow of a third example of the process performed by the radiography device control unit in the radiography system according to this embodiment.

DETAILED DESCRIPTION

Hereinafter, embodiments of the invention will be described in detail with reference to the drawings. The embodiments do not limit the invention.

Figure 1:
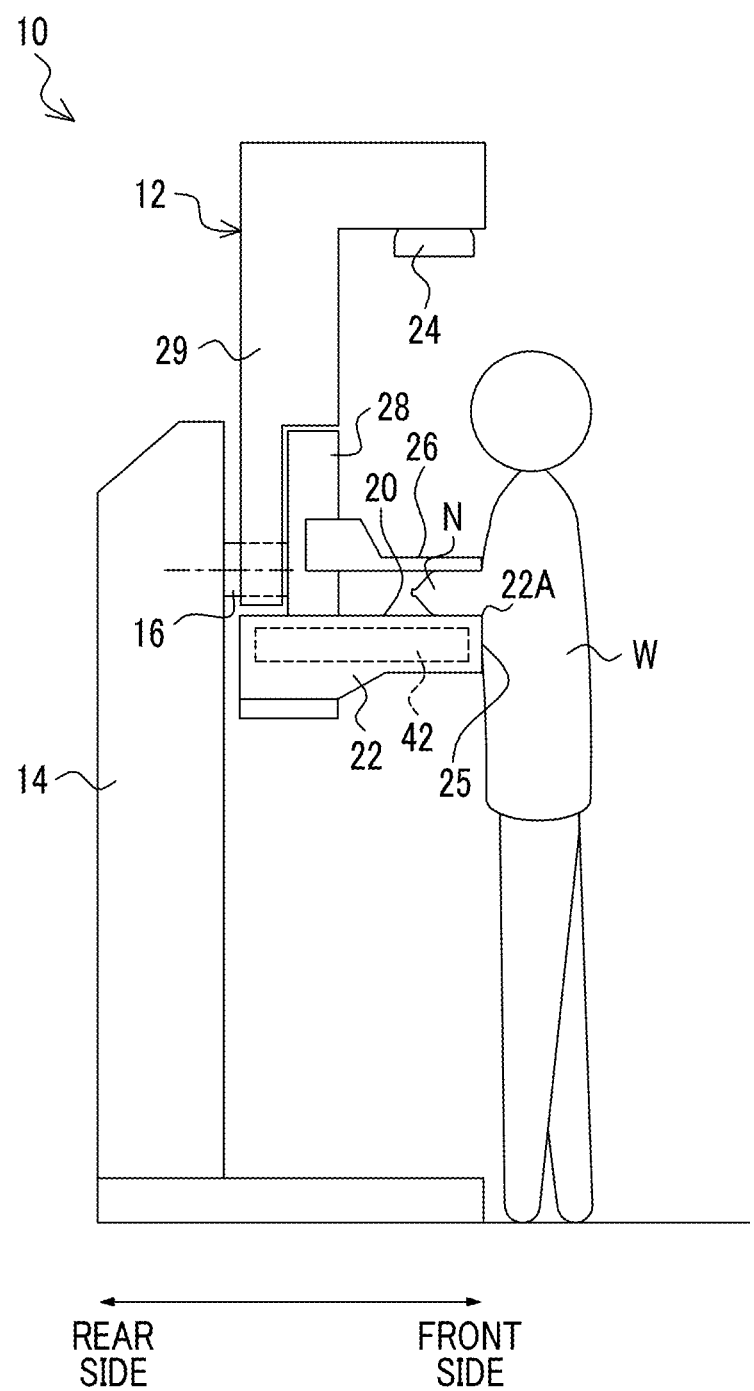
FIG. 1 is a plan view illustrating an example of the structure of a radiography device according to an embodiment.
Figure 2:
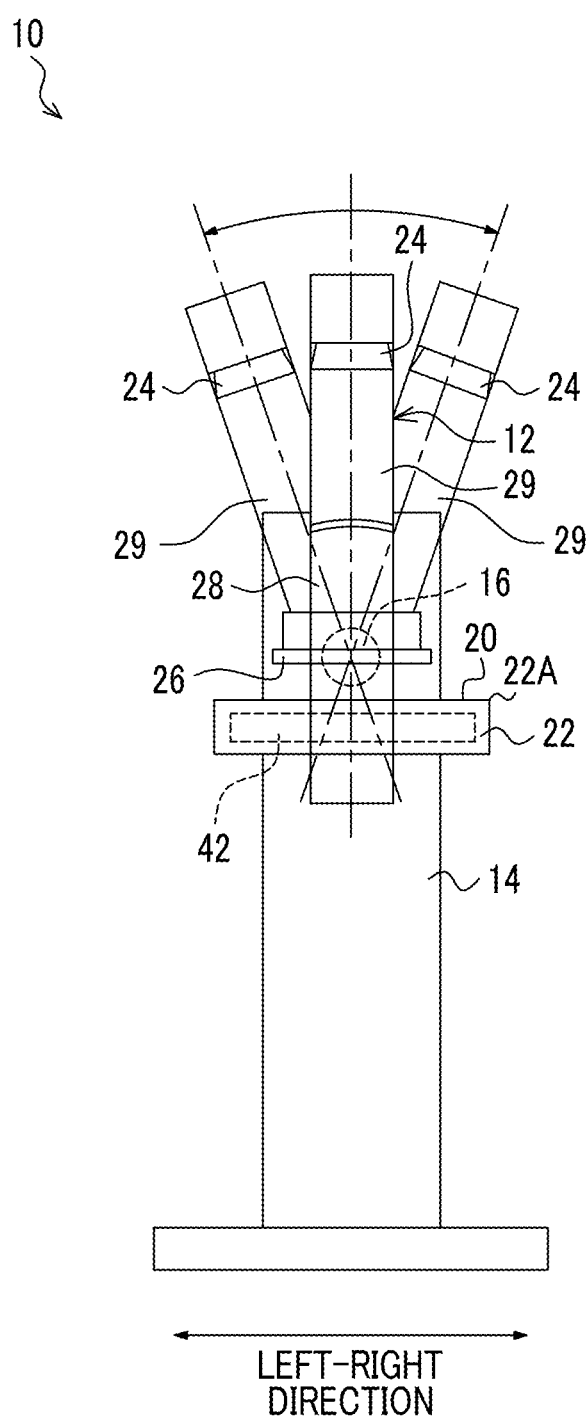
FIG. 2 is a diagram illustrating an example of the structure of the radiography device according to the embodiment during imaging.
Figure 3:
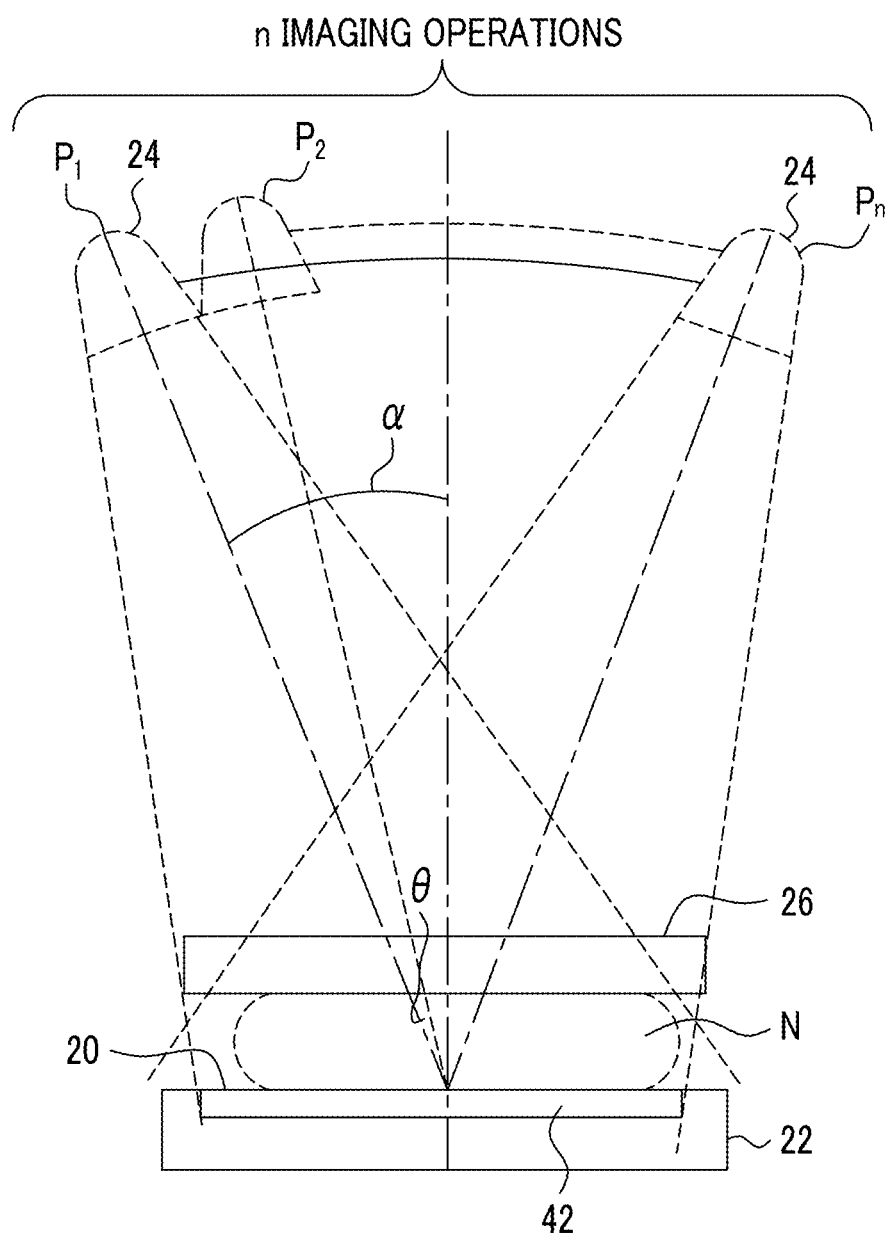
FIG. 3 is a diagram illustrating the operation of the radiography device according to the embodiment during imaging.

As illustrated in FIGS. 1 to 3, a radiography device 10 according to this embodiment captures an image of the breast N of a subject W that stands up as an object, using radiation (for example, X-rays), and is also referred to as, for example, a mammography device. In the following description, a front side which is close to the subject W in a case in which the subject W faces the radiography device 10 during imaging is referred to as the front side of the radiography device 10, a back side which is away from the subject W in a case in which the subject W faces the radiography device 10 is referred to as the rear side of the radiography device 10, and the left-right direction of the subject W in a case in which the subject W faces the radiography device 10 is referred to as the left-right side of the radiography device 10 (see each arrow illustrated in FIGS. 1 and 2).

The imaging target of the radiography device 10 is not limited to the breast N and may be, for example, another part of the body or an object. The radiography device 10 may be a device which captures an image of the breast N of the subject W that sits on a chair (including a car seat) or a device which can individually capture images of the left and right breasts N of the subject W in a state in which at least the upper part of the body of the subject W stands up.

As illustrated in FIG. 1, the radiography device 10 comprises a measurement unit 12 which is provided on the front side of the device and has a substantially C shape in a side view and a base portion 14 which supports the measurement unit 12 from the rear side of the device.

The measurement unit 12 comprises a radiographic stand 22 including a planar imaging surface 20 which comes into contact with the breast N of the subject W that is in a standing state, a compression plate 26 for compressing the breast N against the imaging surface 20 of the radiographic stand 22, and a holding portion 28 which supports the radiographic stand 22 and the compression plate 26. The compression plate 26 is made of a member that transmits radiation. A sensor that detects the position of the compression plate 26 relative to the radiographic stand 22 (particularly, the imaging surface 20) is provided in the holding portion 28. The radiography device 10 can detect the thickness of the breast using the sensor.

In addition, the measurement unit 12 comprises a radiation emitting unit 24 that is provided with a radiation source 30 (see FIG. 4), such as a radiation tube, and emits radiation for examination from the radiation source 30 to the imaging surface 20 and a support portion 29 that is separated from the holding portion 28 and supports the radiation emitting unit 24.

Furthermore, the measurement unit 12 is provided with a rotating shaft 16. Therefore, the measurement unit 12 can be rotated on the base portion 14. The rotating shaft 16 is fixed to the support portion 29. The rotating shaft 16 is rotated integrally with the support portion 29.

Gears are provided in the rotating shaft 16 and the holding portion 28 and switch between an engaged state and a disengaged state. The holding portion 28 can switch between a state in which the holding portion 28 is connected to the rotating shaft 16 and is rotated integrally with the rotating shaft 16 and a state in which the holding portion 28 is separated from the rotating shaft 16 and the rotating shaft 16 rotates idle.

The switching mechanism is not limited to the gear and various types of mechanical elements can be used to switch between the transmission and non-transmission of the torque of the rotating shaft 16.

The holding portion 28 supports the radiographic stand 22 and the radiation emitting unit 24 such that the imaging surface 20 and the radiation emitting unit 24 are spaced at a predetermined distance. The holding portion 28 also supports the compression plate 26 such that the compression plate 26 can slide on the holding portion 28. Therefore, the gap between the compression plate 26 and the imaging surface 20 is variable.

The imaging surface 20 with which the breast N comes into contact is made of carbon in terms of the transmittance or intensity of radiation. A radiation detector 42 that is irradiated with radiation which has passed through the breast N and the imaging surface 20 and detects the radiation is provided in the radiographic stand 22. Image information indicating a radiographic image is generated on the basis of the radiation detected by the radiation detector 42 and a radiographic image is generated by an image processing unit which will be described below. The generation of the radiographic image will be described in detail below.

The radiography device 10 according to this embodiment can irradiate the breast N with radiation at different incident angles (while changing the incident angle) with respect to a detection surface of the radiation detector 42 in a predetermined range and can capture the images of the breast N at different incident angles. Here, the incident angle means an angle formed between a line normal to the detection surface of the radiation detector 42 and a radiation axis. In addition, in this embodiment, the detection surface of the radiation detector 42 is substantially parallel to the imaging surface 20.

In the radiography device 10 according to this embodiment, as illustrated in FIGS. 2 and 3, in a case in which the breast N is irradiated with radiation at different incident angles with respect to the detection surface of the radiation detector 42 in a predetermined range (for example, in a range of ±10° or ±20° with respect to the line normal to the detection surface of the radiation detector 42) to capture the image of the breast N (hereinafter, in some cases, this imaging process is referred to as tomosynthesis imaging and a predetermined range of different incident angles during tomosynthesis imaging is referred to as an incident angle range), the rotating shaft 16 rotates idle with respect to the holding portion 28 such that the radiographic stand 22 and the compression plate 26 do not move and the support portion 29 is rotated such that only the radiation emitting unit 24 is moved in an arc shape. In this embodiment, as illustrated in FIG. 3, the position of the radiation emitting unit 24 is moved from an angle α at a predetermined angular interval of θ and imaging is performed at n positions, that is, positions P1 to Pn of the radiation emitting unit 24. In the following description, the incident angle of radiation in a direction normal to the detection surface of the radiation detector 42 is simply referred to as an "incident angle".

FIGS. 2 and 3 illustrate the posture of the radiography device 10 and the position of the radiation emitting unit 24 during tomosynthesis imaging, respectively. As illustrated in FIGS. 2 and 3, the support portion 29 which supports the radiation emitting unit 24 is inclined and then tomosynthesis imaging is performed.

In general, in a case in which tomosynthesis imaging is performed, the breast N of the subject W is irradiated with radiation n times. Therefore, a dose of radiation is reduced such that an exposure dose does not increase. For example, radiation is emitted such that the total dose of radiation during n irradiation operations is equal to that during general two-dimensional imaging (general imaging in which the subject is irradiated with radiation at a fixed position, without moving the radiation source 30, and then an image of the subject is captured).

The radiography device 10 according to this embodiment can perform both cranio & caudal (CC) imaging and medio-lateral-oblique (MLO) imaging for the breast N. During the CC imaging, the posture of the holding portion 28 is adjusted such that the imaging surface 20 faces the ground in the vertical direction, and the posture of the support portion 29 is adjusted such that the radiation emitting unit 24 is perpendicular to the line normal to the imaging surface 20 (that is, 0°). Then, the radiation emitting unit 24 emits radiation to the breast N in a direction from the head to the feet of the subject W that is in a standing state and the CC imaging is performed. During the MLO imaging, in general, the posture of the holding portion 28 is adjusted, with the radiographic stand 22 rotated at an angle that is equal to or greater than 45° and less than 90°, as compared to the CC imaging, and the holding portion 28 is positioned such that the armpit of the subject W comes into contact with a side wall corner portion 22A of the radiographic stand 22 which is on the front side of the device. Then, the radiation emitting unit 24 emits radiation to the breast N in a direction from the center of the body axis of the subject W to the outside and the MLO imaging is performed.

A chest wall surface 25 with which a chest part below the breast N of the subject W comes into contact during imaging is formed on the surface of the radiographic stand 22 that is disposed on the front side of the device. The chest wall surface 25 has a planar shape.

Figure 4:
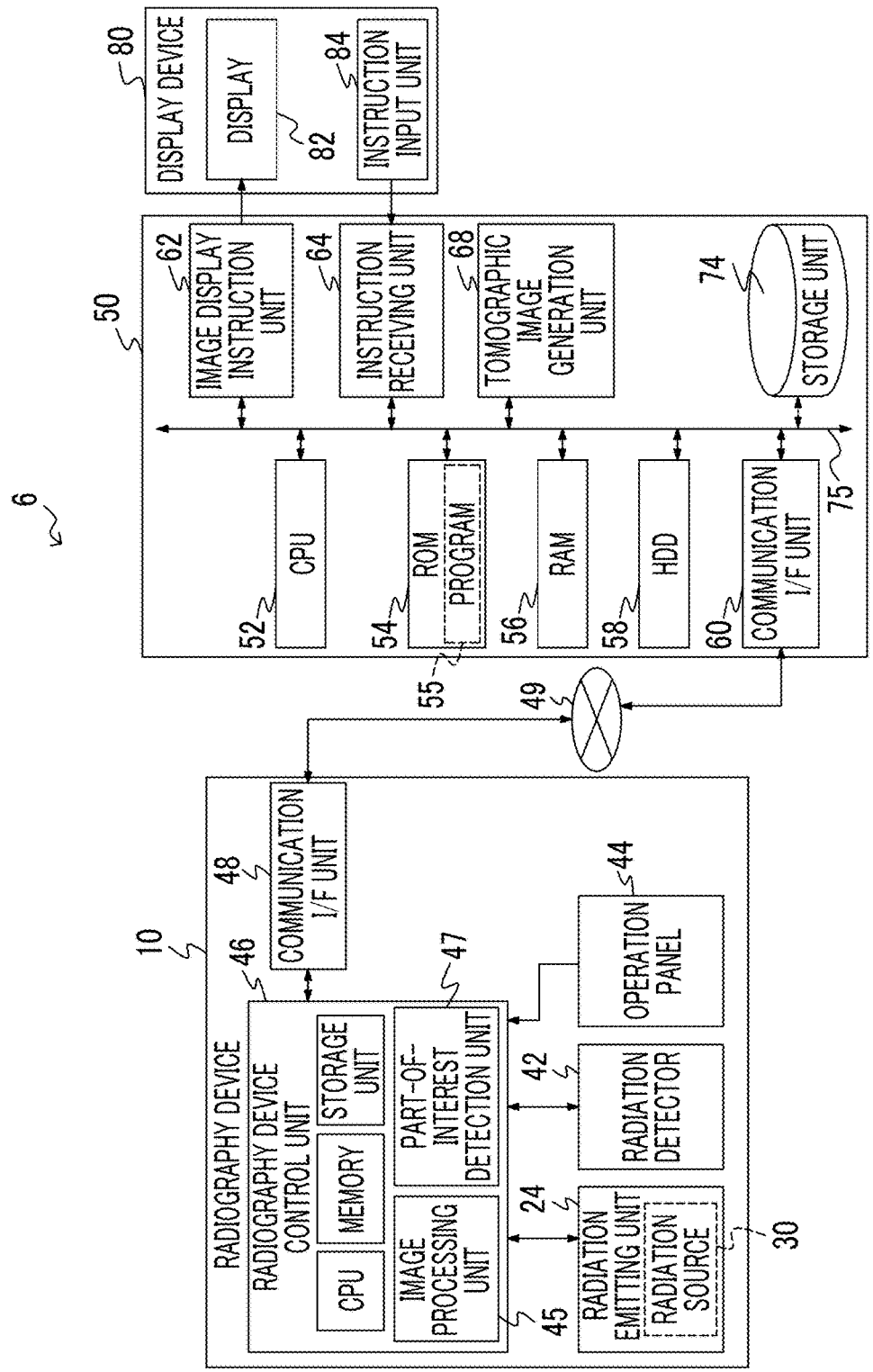
FIG. 4 is a block diagram illustrating an example of the structure of a radiography system according to the embodiment.

FIG. 4 illustrates an example of the structure of a radiography system 6 according to this embodiment.

The radiography system 6 according to this embodiment comprises the radiography device 10, an image processing device 50, and a display device 80.

The radiography device 10 includes the radiation emitting unit 24, the radiation detector 42, an operation panel 44, a radiography device control unit 46, and a communication I/F unit 48.

The radiography device control unit 46 according to this embodiment has a function of controlling the overall operation of the radiography device 10 and comprises a central processing unit (CPU), a memory including a read only memory (ROM) and a random access memory (RAM), and a non-volatile storage unit such as a hard disk drive (HDD) or a flash memory. In this embodiment, the radiography device control unit 46 includes an image processing unit 45 and a part-of-interest detection unit 47. For example, the image processing unit 45 or the part-of-interest detection unit 47 is partially included in, for example, the CPU, the ROM, and the HDD. The radiography device control unit 46 is connected to the radiation emitting unit 24, the radiation detector 42, the operation panel 44, and the communication I/F unit 48.

When an irradiation instruction is received from the operator through an exposure switch displayed on an instruction input unit 84, the radiography device control unit 46 directs the radiation source 30 provided in the radiation emitting unit 24 to emit radiation to the imaging surface 20 according to an imaging menu which is set on the basis of the designated exposure conditions. In this embodiment, the radiation source 30 emits cone beam radiation (for example, a cone-shaped X-ray beam).

A radiographic image generation unit generates a radiographic image of the subject on the basis of radiation that has passed through the subject. In this embodiment, the radiographic image generation unit includes the radiation detector 42 and the image processing unit 45. The radiation detector 42 receives radiation which carries image information, records the image information, and outputs the recorded image information. The radiation detector 42 is, for example, a flat panel detector (FPD) that includes a radiation sensitive layer and converts radiation into digital data. The radiation sensitive layer can be provided substantially in parallel to the imaging surface 20. When radiation is emitted, the radiation detector 42 outputs image information indicating a radiographic image to the image processing unit 45 in the radiography device control unit 46. In this embodiment, the radiation detector 42 receives the radiation which has passed through the breast N and image information indicating a radiographic image is obtained. Then, the image processing unit 45 performs necessary processes, such as a gain correction process, an offset correction process, and a defective pixel correction process, for the image information obtained by the radiation detector 42 to generate a radiographic image. The position of the image processing unit 45 is not limited to that in this embodiment. For example, the image processing unit 45 may be provided in the radiation detector 42. Alternatively, the image processing unit 45 may be provided in the image processing device 50, which will be described below.

The part-of-interest detection unit 47 detects mutation sites including a mutation site that is suspected as a calcification and a mutation site that is suspected as a tumor mass from the radiographic image generated by the image processing unit 45. Information for detecting the mutation site (for example, a threshold value indicating a first size in a predetermined range, which will be described below) is stored in, for example, the memory of the radiography device control unit 46.

In this embodiment, the image processing unit 45 and the part-of-interest detection unit 47 are provided as a portion of the radiography device control unit 46 in the radiography device control unit 46 in order to perform processing at a high speed, without passing through a network 49. However, the invention is not limited thereto. The image processing unit 45 and the part-of-interest detection unit 47 may be implemented by hardware different from the radiography device control unit 46. In a case in which the image processing unit 45 and the part-of-interest detection unit 47 are implemented by different hardware, for example, they may be provided in the image processing device 50. In a case in which the image processing unit 45 and the part-of-interest detection unit 47 are provided in the image processing device 50, information required for the part-of-interest detection unit 47 to detect the mutation site may be stored in, for example, a ROM 54 of the image processing device 50. In addition, the image processing unit 45 and the part-of-interest detection unit 47 may be implemented by hardware, or the CPU may execute software, that is, a program, to implement the image processing unit 45 and the part-of-interest detection unit 47. In this case, the software may be executed by the same computer as that executing software for controlling the overall operation of the imaging device or may be executed by a different computer.

In this embodiment, the radiographic image generation unit can generate radiographic images with different resolutions. Specifically, the radiation detector 42 can generate image information items with a plurality of types of resolutions. More specifically, the radiation detector 42 can perform a process (so-called binning process) which collectively reads information from a plurality of pixels and a process which reads information from each pixel. That is, it is possible to obtain image information indicating radiographic images with two types of resolutions. When the image processing unit 45 performs image processing for the image information, it is possible to finally obtain radiographic images with two types of resolutions. The structure of the radiation detector 42 which can perform the binning process will be described in detail below.

The instruction input unit 84 has a function of setting, for example, various kinds of operation information including imaging conditions and various kinds of operation instructions. The operation panel 44 also has a function which enables a radiologist to move up and down the compression plate 26 to compress the breast of a patient before imaging or inclines the supporting portion 29 (that is, radiation emitting unit 24) in order to perform, for example, CC imaging or MLO imaging. For example, the operation panel 44 is provided as a plurality of switches in the radiographic stand 22 of the radiography device 10. The operation panel 44 may be provided as a touch panel.

The imaging conditions set by the instruction input unit 84 include exposure conditions including a tube voltage, a tube current, and an irradiation time and information such as posture information. In addition, the posture information designated by the instruction input unit 84 includes information indicating imaging positions (including incident angles) in a case in which radiation is incident on the breast N at a plurality of incident angles to capture images.

In addition, for example, the exposure conditions, various kinds of operation information including the posture information, and various kinds of operation instructions may be set by the operator through the instruction input unit 84, may be obtained from other control devices (a radiology information system (RIS) that manages information about, for example, medical examination and diagnosis using radiation), or may be stored in the storage unit in advance.

When various kinds of information are set through the instruction input unit 84, the radiography device control unit 46 directs the radiation emitting unit 24 to emit radiation to the part (breast N), of which the image is to be captured, in the subject W according to the imaging menu which is set on the basis of various kinds of set information, thereby capturing a radiographic image. In a case in which tomosynthesis imaging is performed for the breast N, the radiography device control unit 46 adjusts the posture of the holding portion 28, with the imaging surface 20 up, and adjusts the posture of the support portion 29, with the radiation emitting unit 24 located above the imaging surface 20. Then, as illustrated in FIG. 3, the radiography device control unit 46 rotates the support portion 29 on the basis of the imaging conditions such that the radiation emitting unit 24 is moved from the angle $\alpha$ at an angular interval of $\theta$ in an arch shape and directs the radiation source 30 provided in the radiation emitting unit 24 to emit radiation. In this way, n radiographic images in which the incident angles of radiation are different from each other are obtained.

The communication I/F unit 48 is a communication interface which has a function of receiving and transmitting, for example, the captured radiographic image or various kinds of information between the radiography device 10 and the image processing device 50 through the network 49.

The image processing device 50 has a function (tomographic image generation unit 68) of generating a tomographic image which is reconstructed from the radiographic image acquired from the radiography device 10. In addition, the image processing device 50 has a function (not illustrated) of performing image processing for enabling, for example, a doctor to observe a tomographic image or a projection image displayed on the display device 80. Hereinafter, for example, a person, such as a doctor, who observes the captured radiographic image or the generated tomographic image or diagnoses the mutation site is referred to as a user and the radiographic image which is obtained by the detection of radiation by the radiation detector 42 during tomosynthesis imaging in the radiography device 10 is referred to as a "projection image".

The image processing device 50 comprises a CPU 52, the ROM 54, a RAM 56, an HDD 58, a communication I/F unit 60, an image display instruction unit 62, an instruction receiving unit 64, the tomographic image generation unit 68, and a storage unit 74. These units are connected to each other so as to transmit and receive information through a bus 75 such as a control bus or a data bus.

The CPU 52 controls, for example, the overall operation of the image processing device 50. Specifically, the CPU 52 executes a program 55 (including a program for performing a tomographic image generation process which will be described below) stored in the ROM 54 to perform control. In this embodiment, the program 55 is stored in the ROM 54 in advance. However, the invention is not limited thereto. For example, the program 55 may be stored in a recording medium, such as a CD-ROM or a removable disk, and may be installed from the recording medium to the ROM 54, or may be installed from an external device to the ROM 54 through a communication line such as the Internet. The RAM 56 ensures a work area when the CPU 52 executes the program 55. The HDD 58 stores and retains various kinds of data. In this embodiment, the tomographic image generation unit 68 is provided as a portion of the image processing device 50 in the image processing device 50. However, the invention is not limited thereto. The tomographic image generation unit 68 may be a hardware component different from the image processing device 50.

The communication I/F unit 60 is a communication interface which has a function of transmitting and receiving, for example, the captured radiographic image or various kinds of information between the image processing device 50 and the radiography device 10 through the network 49.

The image display instruction unit 62 has a function of instructing a display 82 of the display device 80 to display a radiographic image.

The display device 80 according to this embodiment has a function of displaying the captured radiographic image and comprises the display 82 on which the radiographic image is displayed and an instruction input unit 84. The instruction input unit 84 may be, for example, a touch panel display, a keyboard, or a mouse. The user (for example, a doctor) can input an instruction related to the display of a radiographic image or the above-mentioned imaging conditions, using the instruction input unit 84. In addition, the user can input an imaging start instruction using the instruction input unit 84. The instruction receiving unit 64 has a function of receiving the instruction which is input from the user through the instruction input unit 84 of the display device 80.

The tomographic image generation unit 68 has a function of reconstructing a plurality of projection images to generate tomographic images that are parallel to the imaging surface 20 at a predetermined slice interval. In this embodiment, the term "parallel" means "substantially parallel" this is a design error.

As described above, in the radiography device 10 according to this embodiment, the breast N is compressed by the compression plate 26 and is fixed while coming into contact with the imaging surface 20 of the radiographic stand 22. Therefore, in the radiography device 10 according to this embodiment, the incident angle of radiation with respect to a direction normal to the detection surface of the radiation detector 42 which is parallel to the imaging surface 20 is equal to the incident angle of radiation with respect to a direction normal to a tomographic plane of the tomographic image of the breast N.

The tomographic image generation unit 68 generates tomographic images from a plurality of projection images, which have been captured with the radiation emitting unit 24 (radiation source 30) moved to positions P1, P2, P3, ..., Pn, at a predetermined slice interval. The projection position of a region of interest on the radiographic image varies depending on the incident angle of radiation with respect to the imaging surface 20. Therefore, the tomographic image generation unit 68 acquires the imaging conditions when the radiographic image is captured by the radiography device 10, calculates the amount of movement of the region of interest in a plurality of radiographic images on the basis of the incident angle of radiation included in the imaging conditions, and reconstructs the tomographic images on the basis of a known reconstruction method such as a shift-and-add method.

In addition to the shift-and-add method, a known CT reconstruction method can be used as the reconstruction method. For example, a filtered back projection (FBP) method which is a representative example of the CT reconstruction method can be used. The FBP method is a reconstruction method which considers parallel plane tomographic scanning in tomographic imaging as a part of cone beam CT scanning and is an expanded version of the filtered back projection method. In addition, the iterative reconstruction method disclosed in JP2011-125698A can be used as the reconstruction method. The iterative reconstruction method is a reconstruction method for CT and can be applied to reconstruction during tomosynthesis imaging, similarly to the FBP method.

The tomographic image generation unit 68 can be implemented by hardware, such as a general electronic circuit, an application specific integrated circuit (ASIC), or a field programmable gate array (FPGA).

The storage unit 74 has a function of storing, for example, image information indicating each of the projection image captured by the radiography device 10 and the tomographic image generated by the tomographic image generation unit 68 and is a large-capacity storage device such as a hard disk. In this embodiment, the storage unit 74 also stores the imaging conditions (for example, the incident angle of radiation) when the radiography device 10 captures a radiographic image.

Figure 5:
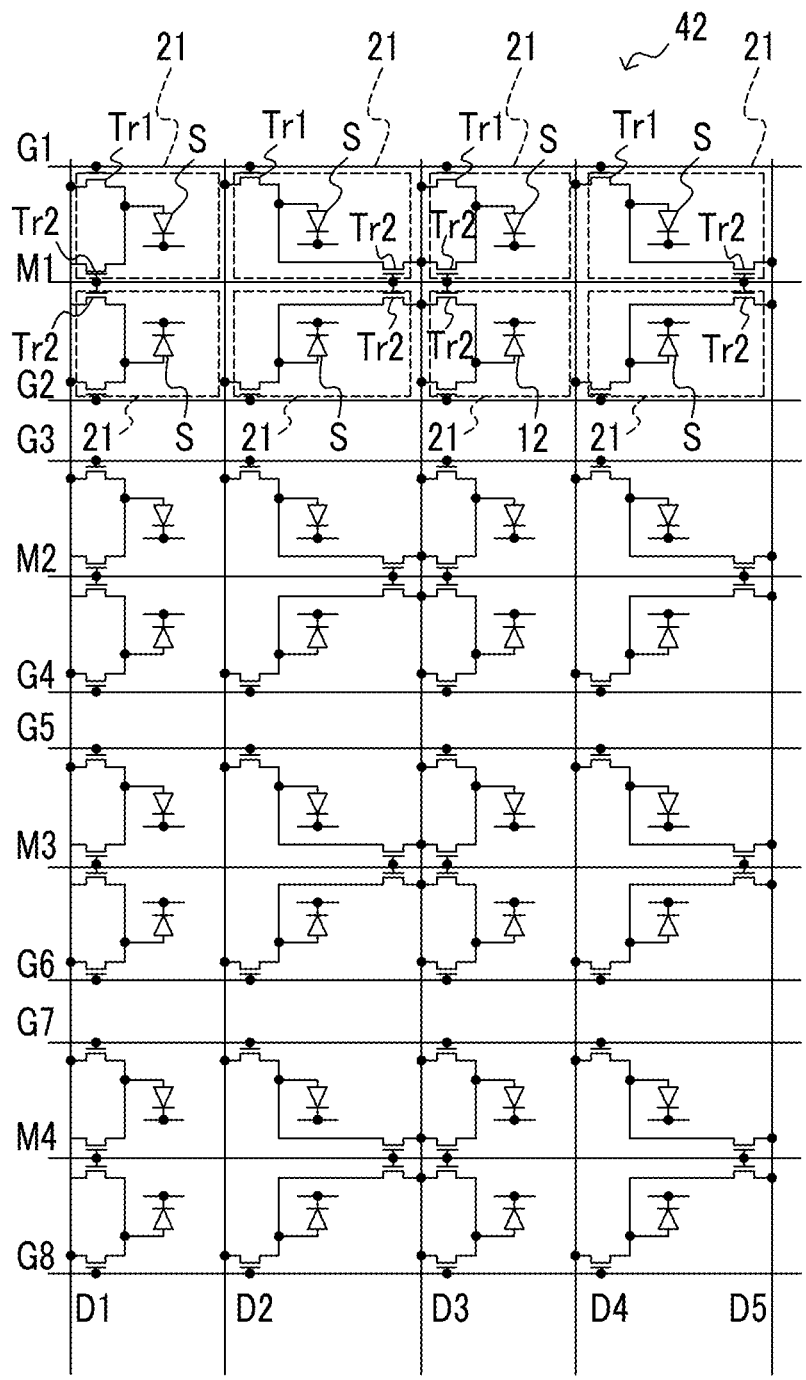
FIG. 5 is a diagram illustrating a first example of the structure of a radiation detector.

Next, an example of the structure of the radiation detector 42 which can perform the binning process will be described. FIG. 5 is a diagram illustrating a first example of the structure of the radiation detector 42.

The radiation detector 42 receives radiation which has passed through the subject and outputs image information indicating a radiographic image of the subject. As illustrated in FIG. 5, the radiation detector 42 includes a scintillator (not illustrated) that receives radiation and emits light and a plurality of pixels 21 each of which includes a sensor unit S that receives the light generated by the scintillator and generates charge and two switching elements (for example, two thin film transistors; hereinafter, simply referred to as transistors) Tr1 and Tr2 that read the charge stored in the sensor unit S. In the radiation detector 42, the plurality of pixels 21 are arranged in a matrix. In addition, the radiation detector 42 includes, for example, a charge amplifier, an A/D converter, and a read control IC which are not illustrated in the drawings. In this embodiment, the radiation detector is an indirect conversion type in which the scintillator converts light according to radiation, the converted light is emitted to the sensor unit S, and charge is generated. However, the invention is not limited thereto. A direct-conversion-type radiation detector includes a charge generation layer (for example, a layer having Se as a main component) that receives radiation and generates charge and a plurality of pixels each of which includes two switching elements that read the charge stored in the charge generation layer.

The plurality of pixels 21 are arranged in a matrix in one direction (a control line direction corresponding to the lateral direction in FIG. 5; hereinafter, also referred to as a "row direction") and a direction (a signal line direction corresponding to the longitudinal direction in FIG. 5; hereinafter, also referred to as a "column direction") intersecting the row direction. In FIG. 5, the arrangement of the pixel 21 is illustrated in brief. For example, 1024×1024 pixels 21 are arranged in the row direction and the column direction.

In the radiation detector 42, a plurality of control lines G (G1 to G8 in FIG. 5) for controlling the turn-on and turn-off of the transistors Tr1 and a plurality of control lines M (M1 to M4 in FIG. 5) for controlling the turn-on and turn-off of the transistors Tr2, and a plurality of signal lines D (D1 to D5 in FIG. 5) which are provided for each column of the pixels 21 for reading the charge stored in the sensor units S alternately intersect each other. The charge of each pixel from the signal line D is transmitted as digital data (that is, an example of image information indicating a radiographic image) to the image processing unit 45 through, for example, a charge amplifier and an A/D converter which are not illustrated.

The sensor unit S of each pixel 21 is provided with a semiconductor layer and a bias electrode that applies a bias voltage to the semiconductor layer. The bias electrode of each pixel is connected to a common line (not illustrated). The bias voltage is applied from a power supply (not illustrated) through the common line.

A control signal for switching (ON/OFF) each transistor Tr1 is supplied to the control line G. As such, when the control signal is supplied to each control line G, each transistor Tr1 is switched (ON/OFF). In addition, a control signal for switching (ON/OFF) each transistor Tr2 is supplied to the control line M. As such, when the control signal is supplied to each control line M, each transistor Tr2 is switched (ON/OFF).

An electric signal corresponding to the amount of charge stored in each pixel 21 is supplied to the signal line D through the transistor Tr1 or the transistor Tr2, according to the switching state (ON/OFF state) of the transistor Tr1 and the switching state (ON/OFF state) of the transistor Tr2 in each pixel 21.

In this embodiment, as illustrated in FIG. 5, in the radiation detector 42, the arrangement of the transistor Tr1, the transistor Tr2, and the sensor unit S in the even-numbered control lines G is reverse to the arrangement of the transistor Tr1, the transistor Tr2, and the sensor unit S in the odd-numbered control lines G (in the vertical direction of FIG. 5).

The radiation detector 42 having the above-mentioned structure can perform imaging with two different types of resolutions. In this embodiment, the higher of two types of resolutions is referred to as high resolution and the lower of two types of resolutions is referred to as low resolution.

That is, in a case in which a high-resolution image is captured, a control signal is input to the control lines M such that the transistors Tr2 are turned off and a control signal is sequentially input to the control lines G such that the transistors Tr1 are turned on. In the pixel 21 in which the transistor Tr1 is turned on, charge is read from the sensor unit S. The charge of one pixel 21 is sequentially output to the signal line D.

In a case in which a low-resolution image is captured, a control signal is input to the control line G such that the transistors Tr1 are turned off and a control signal is sequentially input to the control line M such that each transistor Tr2 is turned on. In the pixel 21 in which the transistor Tr2 is turned on, charge is read from the sensor unit S. Then, the change is output to the signal line D. Therefore, the charges of four pixels 21 are collectively output to one signal line D and are subjected to the subsequent process. Finally, a radiographic image having a lower resolution than that in a case in which the transistor Tr2 is turned off and the transistor Tr1 is turned on is obtained.

Figure 6:
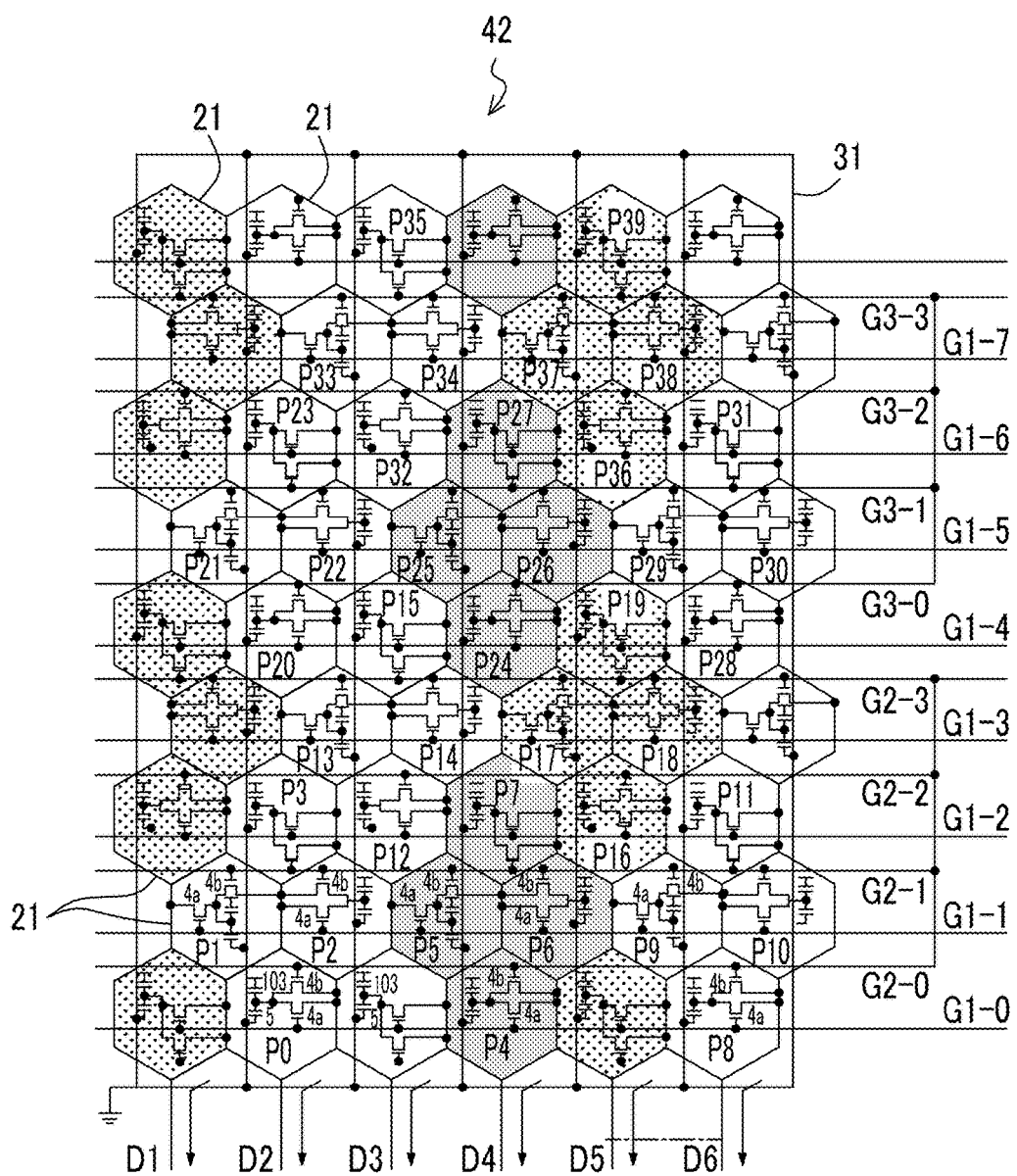
FIG. 6 is a diagram illustrating a second example of the structure of the radiation detector.

Next, another example of the structure of the radiation detector 42 which can perform the binning process will be described. FIG. 6 is a diagram illustrating a second example of the structure of the radiation detector 42.

The radiation detector 42 illustrated in FIG. 6 has the same structure as that illustrated in FIG. 5 except that a plurality of pixels 21, each of which has a hexagonal pixel region, are two-dimensionally arranged in a honeycomb shape while being adjacent to each other and form a region having a substantially rectangular shape as a whole. Each pixel 21 includes a sensor unit 103 that receives light generated by the scintillator and generates charge, a charge storage capacitor 5 that stores the charge generated by the sensor unit 103, and two thin film transistors (hereinafter, simply referred to as transistors) 4a and 4b that read the charge stored in the charge storage capacitor 5.

The pixels 21 are arranged in the honeycomb shape as follows. A first pixel row in which a plurality of pixels 21 that have the same size and have hexagonal pixel regions are arranged in the row direction (the horizontal direction in FIG. 6) and a second pixel row in which a plurality of pixels 21 that have the same size as the pixels 21 in the first pixel row and have hexagonal pixel regions are arranged in the row direction are alternately arranged in a direction intersecting the column direction (the vertical direction in FIG. 6). In addition, the pixels 21 in the second pixel row are arranged between adjacent pixels in the first pixel row so as to correspond thereto and to be shifted by half of the arrangement pitch of the pixels 21 in the first pixel row 21 in the row direction.

The radiation detector 42 comprises first control lines G1-0 to G1-7 corresponding to each pixel row (the first control lines G1-0 to G1-7 are also collectively referred to as first control lines G1. In addition, in a case in which control lines including the other control lines, which will be described below, are generically referred, they are simply referred to as control lines G). The gate electrodes of the transistors 4a provided in each pixel 21 are connected to the first control lines G1. The turn-on and turn-off of the transistors 4a are controlled by signals supplied to the first control lines G1. In addition, the radiation detector 42 comprises second control lines G2-0 to G2-3 which are arranged so as to correspond to each pixel row including the first control lines G1-0 to G1-3 (the second control lines G2-0 to G2-3 are also collectively referred to as second control lines G2) and third control lines G3-0 to G3-3 which are arranged so as to correspond to each pixel row including the first control lines G1-4 to G1-7 (the third control lines G3-0 to G3-3 are also collectively referred to as third control lines G3). The gate electrodes of the transistors 4b that are provided in pixels forming a pixel group, which will be described below, are connected to the second control lines G2 and the third control lines G3. The turn-on and turn-off of the transistors 4b are controlled by signals supplied to the second control lines G2 and the third control lines G3.

As such, the radiation detector 42 has a structure in which a plurality of pixel rows, each of which includes one first control line G1 and one second control line G2, and a plurality of pixel rows, each of which includes one first control line G1 and one third control line G3, are arranged. In addition, the radiation detector 42 comprises a plurality of signal lines D1 to D6 (which are collectively referred to as signal lines D) for reading charge which is generated in the sensor unit 103 of each pixel and is then stored in the charge storage capacitor 5 and a plurality of common (common ground) lines 31. The charge of each pixel transmitted from the signal line D is converted into digital data (that is, an example of image information indicating a radiographic image) by, for example, a charge amplifier and an A/D converter (not illustrated) and is then transmitted to the image processing unit 45.

It is also possible to perform imaging at two different types of resolutions, using the radiation detector 42 illustrated in FIG. 6. Hereinafter, the higher of the two types of resolutions is referred to as high resolution and the lower of the two types of resolutions is referred to as low resolution.

That is, in a case in which a high-resolution image is captured, a control signal for turning off the transistor 4b of each pixel 21 is transmitted to the second control lines G2-0 to G2-3 and the third control lines G3-0 to G3-3. In addition, a control signal is sequentially transmitted from the first control lines G1-0 to G1-7 to the gate of each transistor 4a in order to turn on the transistor 4a of each pixel 21. Then, the transistors 4a of the pixels 21 in each pixel row are sequentially turned on and charge is read from the sensor unit 103 through the transistor 4a. The charge of each signal transmitted from the signal line D is converted into digital data (that is, an example of image information indicating a radiographic image) by, for example, the charge amplifier and the A/D converter (not illustrated). The digital data of each pixel is transmitted to the image processing unit 45 and is subjected to image processing. Finally, a high-resolution radiographic image is obtained.

As such, in the radiation detector 42, a charge signal corresponding to each pixel 21 in each pixel row is transmitted to each of the signal lines D1 to D6 in order to acquire high-resolution image information. In this way, it is possible to obtain image information indicating a radiographic image, using radiation that is emitted to the radiation detector 42.

On the other hand, in a case in which a low-resolution image is captured, the second control lines G2 and the third control lines G3 are used. First, the relationship between each pixel and the second and third control lines G2 and G3 will be described. It is assumed that, among a plurality of pixels 21 illustrated in FIG. 6, for example, four pixels P0 to P3 form a pixel group PG0, four pixels P4 to P7 form a pixel group PG1, four pixels P8 to P11 form a pixel group PG2, four pixels P12 to P15 form a pixel group PG3, and four pixels P16 to P19 form a pixel group PG4. In the five pixel groups, the second control line G2-0 is connected to the gate electrodes of the transistors 4b in the pixel P0 of the pixel group PG0, the pixel P4 of the pixel group PG1, and the pixel P8 of the pixel group PG2. In addition, the second control line G2-1 is connected to the gate electrodes of the transistors 4b in the pixels P1 to P3 of the pixel group PG0, the pixels P5 to P7 of the pixel group PG1, and the pixels P9 to P11 of the pixel group PG2.

Similarly, the second control line G2-2 is connected to the gate electrodes of the transistors 4b in the pixel P12 of the pixel group PG3 and the pixel P16 of the pixel group PG4 and the second control line G2-3 is connected to the gate electrodes in the pixels P13 to P15 of the pixel group PG3 and the pixels P17 to P19 of the pixel group PG4. In the radiation detector 42, the connection between the third control lines G3-0 to G3-3 and the pixel groups (PG5 to PG9) including pixels P20 to P23, pixels P24 to P27, pixels P28 to P31, pixel P32 to P35, and pixels P36 to P39 is the same as the connection between the pixel groups PG0 to PG4 and the second control lines G2-0 to G2-3.

Next, the control of each switching element when a low-resolution image is captured will be described. In a case in which an instruction to capture a low-resolution image is input to the radiation detector 42, a control signal is transmitted from the first control lines G1-0 to G1-7 to the gate electrode of the transistor 4a in each pixel 21 in order to turn off the transistor 4a of each pixel 21.

In addition, a control signal for turning on the corresponding transistors at the same time is transmitted to the second control lines G2-0 to G2-3. As a result, the transistors 4b of all of the pixels 21 in the pixel groups PG0 to PG4 are turned on. Then, the charges stored in the charge storage capacitors 5 of four pixels P0 to P3 in the pixel group PG0 are mixed and a composite charge signal is output to the signal line D2. Similarly, a composite charge signal from four pixels P12 to P15 in the pixel group PG3 is output to the signal line D3. A composite charge signal from four pixels P4 to P7 in the pixel group PG1 is output to the signal line D4. A composite charge signal from four pixels P16 to P19 in the pixel group PG4 is output to the signal line D5. A composite charge signal from four pixels P8 to P11 in the pixel group PG2 is output to the signal line D6.

Then, a control signal for turning on the corresponding transistors at the same time is transmitted to the third control lines G3-0 to G3-3. Then, the transistors 4b of all of the pixels 21 in the pixel groups PG5 to PG9 are turned on. As a result, a composite charge signal from four pixels in the pixel group PG5 is output to the signal line D2. A composite charge signal from four pixels in the pixel group PG8 is output to the signal line D3. A composite charge signal from four pixels in the pixel group PG6 is output to the signal line D4. A composite charge signal from four pixels in the pixel group PG9 is output to the signal line D5. A composite charge signal from four pixels in the pixel group PG7 is output to the signal line D6.

As such, in a case in which a low-resolution image is captured, for each of a plurality of pixel groups, each of which includes four predetermined pixels, among a plurality of pixels 21 forming the radiation detector 42, charges stored in the four pixels are combined (subjected to the binning process) and the charge subjected to the binning process is output to the signal line. This means that, in low-resolution imaging, 2×2 pixel binning is performed in the radiation detector 42 to acquire image information at a speed that is four times higher than that in high-resolution imaging.

In the examples of the structure illustrated in FIGS. 5 and 6, one pixel comprises a plurality of transistors and the reading of charge switches between a mode in which change is read from each pixel and a mode in which charge is collectively read from a plurality of pixels (binning process) to read charge at different resolutions, that is, to acquire image information with different resolutions. However, the acquisition of the image information (or the acquisition of radiographic images) with different resolutions is not limited to the above-mentioned example. For example, as another example, there is a method in which the radiation detector 42 has an internal memory and 2×2 pixel binning is performed using the internal memory. That is, the image information of all of the pixels is read to the internal memory once. In the case of high-resolution imaging, the image information (digital data) of each pixel is transmitted to the image processing unit 45 without any change. In the case of low-resolution imaging, an operation of adding 2×2 pixel information (digital data) is performed using the internal memory and the pixel information is transmitted to the image processing unit 45. In this case, the radiation detector 42 has a structure in which one switching element is provided in each pixel, which is sufficient to achieve low-resolution imaging. In addition, in the case of low-resolution imaging, instead of performing the binning process using the internal memory of the radiation detector 42, a thinning-out process may be performed. In a case in which the thinning-out process is performed in the radiation detector 42, the following methods are used: a method which reads information from only some of a plurality of pixels; and a method which reads information from all of the pixels and outputs information of only one pixel in a unit of 2 pixels×2 pixels from the internal memory of the radiation detector 42 to the image processing unit 45. In addition, the addition (binning process) of the pixel information or the thinning-out process may be performed in the image processing unit 45. That is, the radiographic image generation unit needs to have at least a function of generating radiographic images with different resolutions.

However, in tomosynthesis imaging, the incident angle range is widened to obtain a tomographic image with high resolution (particularly, resolution in a direction normal to the tomographic plane). However, since the incident angle range is widened, the imaging time increases, which results in an increase in burden on the subject. In addition, the resolution of the radiographic image has an effect on the process of the radiographic image generation unit and the processing time of the tomographic image generation unit. Of course, the resolution has an effect on the total time required for the radiation emitting unit to perform a plurality of imaging operations at different incident angles. Therefore, when the time increases, a burden on the subject increases.

For this reason, the radiography device control unit 46 according to this embodiment captures a two-dimensional image before tomosynthesis imaging. It is analyzed whether there is a mutation site in the captured radiographic image. The conditions of tomosynthesis imaging including at least one of resolution or the incident angle range are determined on the basis of the analysis result. Tomosynthesis imaging is performed under the determined imaging conditions. Therefore, tomosynthesis imaging is performed under accurate imaging conditions.

Specifically, in this embodiment, the part-of-interest detection unit 47 of the radiography device control unit 46 detects a mutation site which is suspected as a lesion from a radiographic image obtained by capturing a two-dimensional image before tomosynthesis imaging, using an analysis technique, such as computer aided diagnosis (CAD). Then, the radiography device control unit 46 determines the conditions of tomosynthesis imaging on the basis of whether there is a mutation site.

In particular, in this embodiment, the part-of-interest detection unit 47 of the radiography device control unit 46 can detect whether the detected mutation site is a mutation site suspected as a calcification or a mutation site suspected as a tumor mass, on the basis of the size of the detected mutation site. Specifically, the part-of-interest detection unit 47 has a radiographic image analysis function, such as CAD, and can detect the candidates of an abnormal shadow as the mutation site from the radiographic image. In addition, the part-of-interest detection unit 47 includes a size detection unit that detects the size of the mutation site. For example, the size detection unit detects the maximum diameter of a circle that is circumscribed about the mutation site as the size of the mutation site. In a case in which the size of the mutation site detected by the size detection unit is a first size (for example, equal to or greater than several pixels and equal to or less than 10 pixels) in a predetermined range, the part-of-interest detection unit 47 detects the mutation site as a mutation site that is suspected as a calcification. In a case in which the size of the mutation site is greater than the first size (for example, greater than 10 pixels), the part-of-interest detection unit 47 detects the mutation site as a mutation site that is suspected as a tumor mass. In other words, the part-of-interest detection unit 47 can detect, as the mutation site, a part having a size that is equal to or greater than the first size (for example, equal to or greater than several pixels) in the predetermined range. The "first size in a predetermined range" and the "size greater than the first size", and the "size equal to or greater than the first size in a predetermined range" will be described in detail below. The "first size in a predetermined range" indicates a limited range having an upper limit and a lower limit. When a pixel is used as a unit, the "first size in a predetermined range" indicates, for example, a range from several pixels to 10 pixels. When a meter is used as a unit, the "first size in a predetermined range" indicates a range from 100 μm to 1 mm. The "size greater than the first size" means that at least a lower limit is set and the size is greater than the lower limit. The lower limit is an upper limit designated by the "first size in a predetermined range". For example, when the upper limit of the "first size in a predetermined range" is 10 pixels, the "size greater than the first size" means that the size is greater than 10 pixels. In addition, the "size greater than the first size" may indicate a range from 10 pixels to 1000 pixels. That is, when the range of the "size greater than the first size" is set, the upper limit of the range may or may not be set. Finally, the "size equal to or greater than the first size in a predetermined range" is a rough range satisfying the "first size in a predetermined range" and the "size greater than the first size". Specifically, the "size equal to or greater than the first size in a predetermined range" means that at least a lower limit is set and the size is greater than the lower limit. The lower limit is a lower limit designated by the "first size in a predetermined range". For example, when the lower limit set by the "first size in a predetermined range" is several pixels, the "size equal to or greater than the first size in a predetermined range" means that the size is equal to or greater than several pixels. The range of the mutation site having the same size as a boundary value of the upper limit or the lower limit is not limited to the above description. In this embodiment, the size detected by the size detection unit is the maximum diameter which is a one-dimensional length. However, the invention is not limited thereto. The size may be a two-dimensional size such as the number of pixels or an area. In this case, the number of pixels or an area is used as the boundary value.

The radiography device control unit 46 (part-of-interest detection unit 47) detects the mutation site, using, for example, the technique disclosed in JP2011-120747A. When the candidates of an abnormal shadow (mutation site) in the breast are detected on the basis of the captured radiographic image, it is possible to detect the candidates of the abnormal shadow (mutation site), using a method using an iris filtering process (also see JP1998-97624A (JP-H10-97624A)) or a method using a morphological filter (also see JP1996-294479A (JP-H08-294479A)), as described in JP2011-120747A.

In this embodiment, the radiography device 10 can generate radiographic images with two types of resolutions and can move the radiation emitting unit 24 in two types of incident angle ranges. These functions are used in tomosynthesis imaging and may also be used in a first imaging process which will be described below. Hereinafter, the higher of the two types of resolutions is referred to as high resolution and the lower of the two types of resolutions is referred to as low resolution. In addition, the narrower of the two types of incident angle ranges is referred to as a narrow incident angle range and the wider of the two types of incident angle ranges is referred to as a wide incident angle range. For example, a value, such as the incident angle range, is stored in the memory of the radiography device control unit 46 in advance.

In this embodiment, the radiography device control unit 46 controls tomosynthesis imaging such that tomosynthesis imaging is performed under first conditions of low resolution and a narrow incident angle range in a case in which a mutation site that is suspected as a lesion has not been detected by the radiography device control unit 46 (part-of-interest detection unit 47) and tomosynthesis imaging is performed under second conditions which are different from the first conditions in at least one of the resolution or the incident angle range in a case in which the mutation site that is suspected as a lesion has been detected.

Specifically, as illustrated in FIGS. 7A and 7B, imaging conditions, such as resolution and the incident angle range, are designated and tomosynthesis imaging is performed in each of the following cases: a case in which a mutation site that is suspected as a lesion has not been detected by image analysis such as CAD; a case in which a calcified part has been detected as the mutation site by image analysis such as CAD; a case in which a tumor mass part has been detected as the mutation site by image analysis such as CAD; and a case in which both the calcification and the tumor mass have been detected as the mutation site.

In the example illustrated in FIG. 7A, in a case in which no mutation site has been detected, tomosynthesis imaging is performed under the conditions of low resolution and a narrow incident angle range. In a case in which a calcification has been detected, tomosynthesis imaging is performed under the conditions of high resolution and a narrow incident angle range since a mutation site, such as the calcification, tends to be small. In a case in which a tumor mass has been detected, tomosynthesis imaging is performed under the conditions of low resolution and a wide incident angle range since the tumor mass is larger than the calcification. In a case in which both the calcification and the tumor mass have been detected, tomosynthesis imaging is performed under the conditions of high resolution and a wide incident angle range.

In addition, tomosynthesis imaging may be performed as in the example illustrated in FIG. 7B. That is, tomosynthesis imaging is performed by the same method as that in the example illustrated in FIG. 7A except in the case in which a tumor mass has been detected. In a case in which a tumor mass has been detected, tomosynthesis imaging is performed under the conditions of high resolution and a wide incident angle range, similar to the case in which both the calcification and the tumor mass have been detected as illustrated in FIG. 7A.

Alternatively, tomosynthesis imaging may be performed as in the case illustrated in FIG. 7C. That is, in a case in which no mutation site has been detected, tomosynthesis imaging is performed under the conditions of low resolution and a narrow incident angle range. In a case in which a mutation site, such as a calcification or a tumor mass, has been detected, tomosynthesis imaging is performed under the conditions of high resolution and a wide incident angle range. In the example illustrated in FIG. 7C, the mutation site is not limited to the calcification or the tumor mass. Even in a case in which other types of mutation sites have been extracted, tomosynthesis imaging may be performed under the conditions of high resolution and a wide incident angle range.

In this embodiment, the part-of-interest detection unit 47 of the radiography device control unit 46 detects a mutation site that is suspected as a lesion. However, for example, in a case in which the part-of-interest detection unit 47 has a low processing capability, the image processing device 50 may have the functions of the part-of-interest detection unit 47. In this embodiment, among the conditions of tomosynthesis imaging, for example, an exposure condition determining method may be performed as follows. That is, the radiography device control unit 46 analyzes the shade of a two-dimensional image captured before tomosynthesis imaging. Then, an irradiation dose in tomosynthesis imaging may be determined such that the shade of the projection image obtained by tomosynthesis imaging falls within a predetermined range.

Next, the operation of the radiography system 6 having the above-mentioned structure in the examples illustrated in FIGS. 7A to 7C will be described.

First, the operation of the radiography system 6 will be described, using the case illustrated in FIG. 7A as a first example. FIG. 8 is a flowchart illustrating an example of the flow (radiography method) of the process of the first example performed by the radiography device control unit 46 in the radiography system 6 according to this embodiment.

The user brings the breast N of the subject W into contact with the imaging surface 20 of the radiography device 10. In this state, when the user inputs an operation instruction to start compression, the radiography device 10 moves the compression plate 26 to the imaging surface 20 so as to compress the breast N in Step 100.

Then, in Step 102, before tomosynthesis imaging which will be described below, a first imaging process which acquires a two-dimensional image (radiographic image) of the breast N is performed. The first imaging process is performed, with the radiation emitting unit 24 being inclined at a first predetermined incident angle with respect to the breast N. Specifically, with the radiation emitting unit 24 being vertically located with respect to the radiographic stand 22 (a central position in FIG. 2), the image of the breast N is captured with a radiation dose which has been determined on the basis of the thickness of the breast N detected by the radiography device 10. In general, when the thickness of the breast N is large, the amount of radiation which reaches the radiation detector 42 (passes through the breast N) is reduced. Therefore, in this embodiment, a correspondence relationship among the first incident angle, the thickness of the breast N, and a radiation dose is stored in the memory of the radiography device control unit 46 in advance. In this embodiment, the radiation detector 42 outputs high-resolution image information, without performing the binning process. However, the radiation detector 42 may perform the binning process. Then, the image processing unit 45 performs necessary processes, such as a gain correction process, an offset correction process, and a defective pixel correction process, for the image information of the breast N obtained by the radiation detector 42 to generate a radiographic image of the breast N (for example, a RAW format is applied as the format of the image).

In Step 104, the part-of-interest detection unit 47 of the radiography device control unit 46 analyzes the radiographic image generated by the image processing unit 45. The part-of-interest detection unit 47 detects a mutation site that is suspected as a lesion. Then, the process proceeds to Step 106.

In Step 106, the radiography device control unit 46 (part-of-interest detection unit 47) determines whether a mutation site suspected as a lesion has been detected. In the determination, the radiography device control unit 46 (the part-of-interest detection unit 47, particularly, the size detection unit) determines whether a mutation site with a size that is equal to or greater than the first size in the predetermined range has been detected. In a case in which the determination result is "No", the process proceeds to Step 108. In a case in which the determination result is "Yes", the process proceeds to Step 110.

In Step 108, the radiography device control unit 46 performs control such that low resolution and a narrow incident angle range are set as the conditions of tomosynthesis imaging. Specifically, the radiography device control unit 46 performs control such that the radiation detector 42 performs the binning process and the incident angle range during the acquisition of the projection image of the breast is set to a narrow incident angle range. As such, since an image is captured at low resolution, for example, the time required for image processing is shorter than that when an image is captured at high resolution. In addition, since the incident angle range is set to a narrow incident angle range during tomosynthesis imaging, an imaging time is shorter than that when an image is captured in a wide incident angle range. Therefore, in a case in which no mutation site has been detected, it is possible to reduce a burden on the subject W caused by the compression of the breast N during imaging. After the tomosynthesis imaging conditions are set, the process proceeds to Step 120.

In Step 110, the radiography device control unit 46 (part-of-interest detection unit 47) determines whether only a calcification has been detected. For example, in a case in which a mutation site having the first size in the predetermined range has been detected, it is determined that the mutation site is suspected as a calcification. In a case in which only the mutation site suspected as a calcification has been detected, that is, the determination result is "Yes", the process proceeds to Step 112. In a case in which the determination result is "No", the process proceeds to Step 114.

In Step 112, the radiography device control unit 46 performs control such that high resolution and a narrow incident angle range are set as the conditions of tomosynthesis imaging. That is, the radiography device control unit 46 performs control such that the radiation detector 42 does not perform the binning process and the incident angle range during the acquisition of the projection image of the breast is set to a narrow incident angle range. As such, in a case in which only the mutation site suspected as a calcification has been detected, an image is captured at high resolution since the calcification is smaller than a mutation site suspected as a tumor mass. In addition, since the imaging range is limited, tomosynthesis imaging is performed in a narrow incident angle range. Therefore, it is possible to obtain a necessary projection image and a necessary tomographic image. After the tomosynthesis imaging conditions are set, the process proceeds to Step 120.

In Step 114, the radiography device control unit 46 (part-of-interest detection unit 47) determines whether only a tumor mass has been detected. For example, in a case in which the size of the detected mutation site is greater than the first size in the predetermined range, it is determined that the mutation site is suspected as a tumor mass. In a case in which only the mutation site suspected as a tumor mass has been detected, that is, the determination result is "Yes", the process proceeds to Step 116. In a case in which the determination result is "No", in this embodiment, it is determined that both the mutation site suspected as a calcification and the mutation site suspected as a tumor mass have been detected and the process proceeds to Step 118.

In Step 116, the radiography device control unit 46 performs control such that low resolution and a wide incident angle range are set as the conditions of tomosynthesis imaging. That is, the radiography device control unit 46 performs control such that the radiation detector 42 performs the binning process and the incident angle range during the acquisition of the projection image of the breast is set to a wide incident angle range. As such, in a case in which only the mutation site suspected as a tumor mass has been detected, an image is captured at low resolution since an imaging target is larger than a calcification. Therefore, the processing time is reduced. In addition, tomosynthesis imaging is performed in a wide incident angle range. Therefore, it is possible to obtain a necessary projection image and a necessary tomographic image. After the tomosynthesis imaging conditions are set, the process proceeds to Step 120.

In Step 118, the radiography device control unit 46 performs control such that high resolution and a wide incident angle range are set as the conditions of tomosynthesis imaging. That is, the radiography device control unit 46 performs control such that the radiation detector 42 does not perform the binning process and the incident angle range during the acquisition of the projection image of the breast is set to a wide incident angle range. As such, in a case in which both the mutation site suspected as a calcification and the mutation site suspected as a tumor mass have been detected, tomosynthesis imaging is performed under the conditions of high resolution and a wide incident angle range to obtain a necessary projection image and a necessary tomographic image.

In Step 120, tomosynthesis imaging is performed under the set tomosynthesis imaging conditions. That is, the supporting portion 29 is moved to the maximum angle in the set incident angle range and tomosynthesis imaging starts. For example, imaging is performed while the supporting portion 29 is moved at an angular interval of 1°. In this way, a plurality of projection images corresponding to the set incident angle range are captured. The capture of a radiographic image at each position will be described in detail below. The image processing unit 45 performs necessary processes, such as a gain correction process, an offset correction process, and a defective pixel correction process, for the image information obtained by the radiation detector 42, in which whether to perform the binning process is set, to generate a radiographic image (projection image) with, for example, a RAW format. After tomosynthesis imaging is completed, the fixation of the breast by the compression plate 26 is released. For example, the compression plate 26 is moved in a direction in which it becomes further away from the imaging surface 20 to release the fixation of the breast. Then, the process proceeds to Step 122.

In Step 122, the captured radiographic image is output to the image processing device 50 and the process of the radiography device control unit 46 during imaging ends. Then, in the image processing device 50, the tomographic image generation unit 68 performs image processing, such as FBP, on the basis of the projection image output from the radiography device control unit 46 to generate a tomographic image. The radiography device 10 according to this embodiment is an intelligent device that can perform the detection of a mutation site from a captured two-dimensional image, the setting of tomosynthesis imaging conditions, and tomosynthesis imaging, using only one process of compressing the breast N.

As such, a mutation site is detected from the radiographic image (that is, the two-dimensional image of the breast obtained by the first imaging process) captured before tomosynthesis imaging, the conditions of tomosynthesis imaging are determined on the basis of the detection result, and tomosynthesis imaging is performed. Therefore, it is possible to obtain an accurate radiographic image while reducing a burden on the subject.

Figure 9:
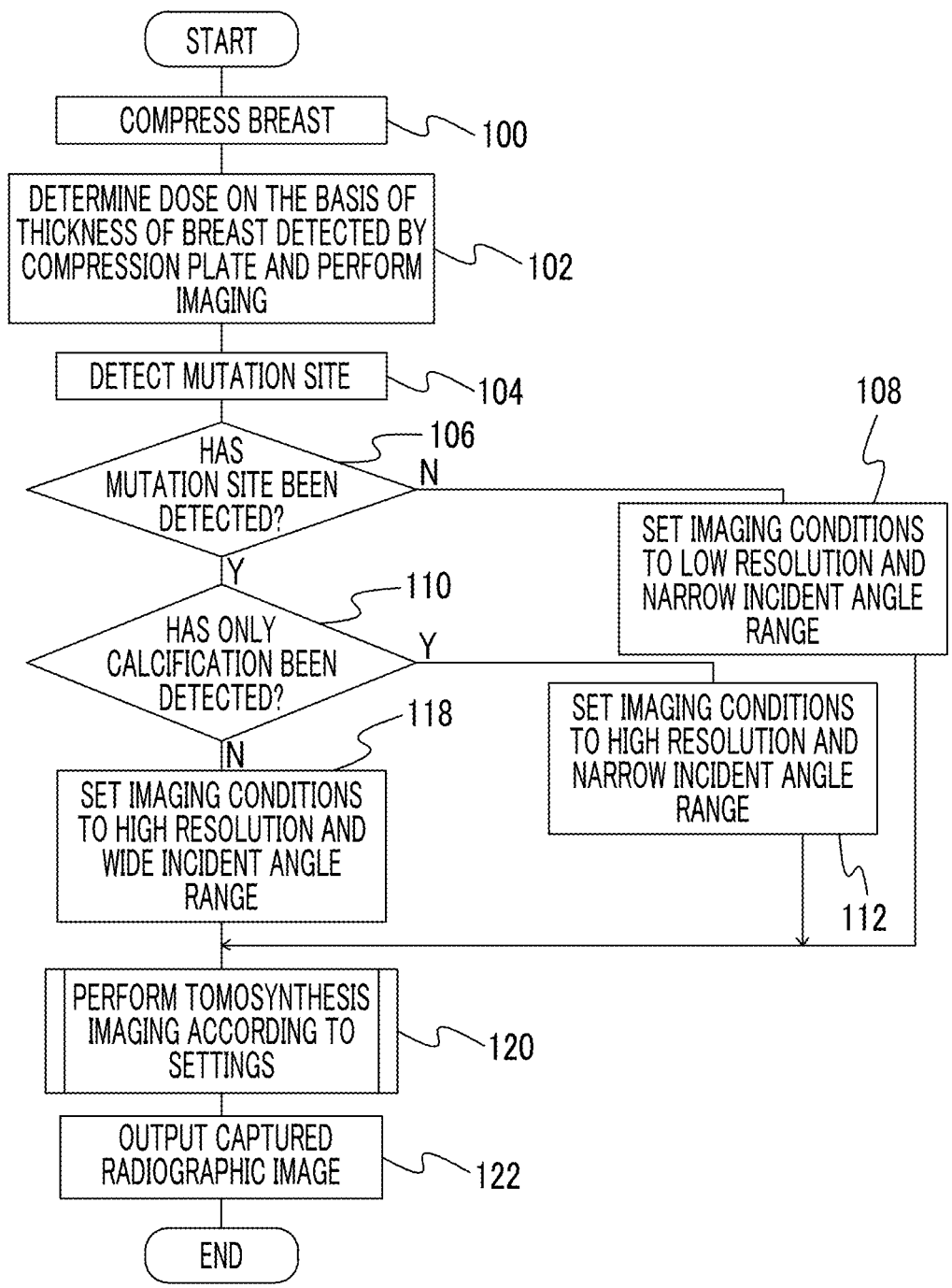
FIG. 9 is a flowchart illustrating an example of the flow of a second example of the process performed by the radiography device control unit in the radiography system according to this embodiment.

Next, the operation of the radiography system 6 will be described, using the case illustrated in FIG. 7B as a second example. FIG. 9 is a flowchart illustrating an example of the flow (radiography method) of the process of the second example performed by the radiography device control unit 46 in the radiography system 6 according to this embodiment. In the second example, the same steps as those in the first example are denoted by the same reference numerals.

The user brings the breast N of the subject W into contact with the imaging surface 20 of the radiography device 10. In this state, when the user inputs an operation instruction to start compression, the radiography device 10 moves the compression plate 26 to the imaging surface 20 so as to compress the breast N in Step 100.

Then, in Step 102, before tomosynthesis imaging which will be described below, a first imaging process which acquires a two-dimensional image (radiographic image) of the breast N is performed. The first imaging process is performed, with the radiation emitting unit 24 being inclined at a first predetermined incident angle with respect to the breast N. Specifically, with the radiation emitting unit 24 being vertically located with respect to the radiographic stand 22 (a central position in FIG. 2), the image of the breast N is captured with a radiation dose which has been determined on the basis of the thickness of the breast N detected by the radiography device 10. In general, when the thickness of the breast N is large, the amount of radiation which reaches the radiation detector 42 (passes through the breast N) is reduced. Therefore, in this embodiment, a correspondence relationship among the first incident angle, the thickness of the breast N, and a radiation dose is stored in the memory of the radiography device control unit 46 in advance. In this embodiment, the radiation detector 42 outputs high-resolution image information, without performing the binning process. However, the radiation detector 42 may perform the binning process. Then, the image processing unit 45 performs necessary processes, such as a gain correction process, an offset correction process, and a defective pixel correction process, for the image information of the breast N obtained by the radiation detector 42 to generate a radiographic image of the breast N (for example, a RAW format is applied as the format of the image). In addition, for example, the conditions of the subsequent tomosynthesis imaging are determined on the basis of the result of the first imaging process.

In Step 104, the part-of-interest detection unit 47 of the radiography device control unit 46 analyzes the radiographic image generated by the image processing unit 45. The part-of-interest detection unit 47 detects a mutation site that is suspected as a lesion. Then, the process proceeds to Step 106.

In Step 106, the radiography device control unit 46 (part-of-interest detection unit 47) determines whether a mutation site suspected as a lesion has been detected. In the determination, the radiography device control unit 46 (the part-of-interest detection unit 47, particularly, the size detection unit) determines whether a mutation site with a size that is equal to or greater than the first size in the predetermined range has been detected. In a case in which the determination result is "No", the process proceeds to Step 108. In a case in which the determination result is "Yes", the process proceeds to Step 110.

In Step 108, the radiography device control unit 46 performs control such that low resolution and a narrow incident angle range are set as the conditions of tomosynthesis imaging. Specifically, the radiography device control unit 46 performs control such that the radiation detector 42 performs the binning process and the incident angle range during the acquisition of the projection image of the breast is set to a narrow incident angle range. As such, since an image is captured at low resolution, for example, the time required for image processing is shorter than that when an image is captured at high resolution. In addition, since the incident angle range is set to a narrow incident angle range during tomosynthesis imaging, an imaging time is shorter than that when an image is captured in a wide incident angle range. Therefore, in a case in which no mutation site has been detected, it is possible to reduce a burden on the subject W caused by the compression of the breast N during imaging. After the tomosynthesis imaging conditions are set, the process proceeds to Step 120.

In Step 110, the radiography device control unit 46 (part-of-interest detection unit 47) determines whether only a calcification has been detected. For example, in a case in which a mutation site having the first size in the predetermined range has been detected, it is determined that the mutation site is suspected as a calcification. In a case in which only the mutation site suspected as a calcification has been detected, that is, the determination result is "Yes", the process proceeds to Step 112. In a case in which the determination result is "No", the process proceeds to Step 118.

In Step 112, the radiography device control unit 46 performs control such that high resolution and a narrow incident angle range are set as the conditions of tomosynthesis imaging. That is, the radiography device control unit 46 performs control such that the radiation detector 42 does not perform the binning process and the incident angle range during the acquisition of the projection image of the breast is set to a narrow incident angle range. As such, in a case in which only the mutation site suspected as a calcification has been detected, an image is captured at high resolution since the calcification is smaller than a mutation site suspected as a tumor mass. In addition, since the imaging range is limited, tomosynthesis imaging is performed in a narrow incident angle range. Therefore, it is possible to obtain a necessary projection image and a necessary tomographic image. After the tomosynthesis imaging conditions are set, the process proceeds to Step 120.

In Step 118, the radiography device control unit 46 performs control such that high resolution and a wide incident angle range are set as the conditions of tomosynthesis imaging. That is, the radiography device control unit 46 performs control such that the radiation detector 42 does not perform the binning process and the incident angle range during the acquisition of the projection image of the breast is set to a wide incident angle range. As such, in a case in which the detected mutation site is not only a mutation site that is suspected as a calcification (this case includes a case in which it is determined that only a mutation site that is suspected as a tumor mass has been detected and a case in which both a mutation site that is suspected as a calcification and a mutation site that is suspected as a tumor mass have been detected), tomosynthesis imaging is performed under the conditions of high resolution and a wide incident angle range to obtain a necessary projection image and a necessary tomographic image.

That is, in the process according to the second example, the radiography device control unit 46 (part-of-interest detection unit 47) detects a mutation site. In a case in which only a mutation site that is suspected as a calcification has not been detected (this case includes a case in which it is determined that only a mutation site that is suspected as a tumor mass has been detected and a case in which it is determined that both a mutation site that is suspected as a calcification and a mutation site that is suspected as a tumor mass have been detected), that is, the determination result in Step 110 is "No", the process proceeds to Step 118 and high resolution and a wide incident angle range are set.

Therefore, in the process according to the second example, even in a case in which only a mutation site suspected as a tumor mass is present, tomosynthesis imaging is performed under the conditions of high resolution and a wide incident angle range to obtain a necessary projection image and a necessary tomographic image. Furthermore, even in a case in which both a mutation site suspected as a calcification and a mutation site suspected as a tumor mass are present, tomosynthesis imaging is performed under the conditions of high resolution and a wide incident angle range to obtain a necessary projection image and a necessary tomographic image.

In Step 120, tomosynthesis imaging is performed under the set tomosynthesis imaging conditions. That is, the supporting portion 29 is moved to the maximum angle in the set incident angle range and tomosynthesis imaging starts. For example, imaging is performed while the supporting portion 29 is moved at an angular interval of 1°. In this way, a plurality of projection images corresponding to the set incident angle range are captured. The capture of a radiographic image at each position will be described in detail below. The image processing unit 45 performs necessary processes, such as a gain correction process, an offset correction process, and a defective pixel correction process, for the image information obtained by the radiation detector 42, in which whether to perform the binning process is set, to generate a radiographic image (projection image) with, for example, a RAW format. After tomosynthesis imaging is completed, the fixation of the breast by the compression plate 26 is released. For example, the compression plate 26 is moved in a direction in which it becomes further away from the imaging surface 20 to release the fixation of the breast. Then, the process proceeds to Step 122.

In Step 122, the captured radiographic image is output to the image processing device 50 and the process of the radiography device control unit 46 during imaging ends. Then, in the image processing device 50, the tomographic image generation unit 68 performs image processing, such as FBP, on the basis of the projection image output from the radiography device control unit 46 to generate a tomographic image. The radiography device 10 according to this embodiment is an intelligent device that can perform the detection of a mutation site from a captured two-dimensional image, the setting of tomosynthesis imaging conditions, and tomosynthesis imaging, using only one process of compressing the breast N.

That is, in the process according to the first example, in a case in which only the mutation site suspected as a tumor mass has been detected, the conditions of tomosynthesis imaging are set to low resolution and a wide incident angle range. However, in the process according to the second example, in a case in which only the mutation site suspected as a tumor mass has been detected, the conditions of tomosynthesis imaging are set to high resolution and a wide incident angle range. In the process according to the second example, similarly to the process according to the first example, a mutation site is detected from the radiographic image (that is, the two-dimensional image of the breast obtained by the first imaging process) captured before tomosynthesis imaging, the conditions of tomosynthesis imaging are determined on the basis of the detection result, and tomosynthesis imaging is performed. Therefore, it is possible to obtain an accurate projection image and an accurate tomographic image while reducing a burden on the subject.

The user may set in advance whether to set the conditions of tomosynthesis imaging as in the first example or as in the second example in a case in which only the mutation site suspected as a tumor mass has been detected.

Next, the operation of the radiography system 6 will be described, using the case illustrated in FIG. 7C as a third example. FIG. 10 is a flowchart illustrating an example of the flow (radiography method) of the process of the third example performed by the radiography device control unit 46 in the radiography system 6 according to this embodiment. In the third example, the same steps as those in the first example are denoted by the same reference numerals.

The user brings the breast N of the subject W into contact with the imaging surface 20 of the radiography device 10. In this state, when the user inputs an operation instruction to start compression, the radiography device 10 moves the compression plate 26 to the imaging surface 20 so as to compress the breast N in Step 100.

Then, in Step 102, before tomosynthesis imaging which will be described below, a first imaging process which acquires a two-dimensional image (radiographic image) of the breast N is performed. The first imaging process is performed, with the radiation emitting unit 24 being inclined at a first predetermined incident angle with respect to the breast N. Specifically, with the radiation emitting unit 24 being vertically located with respect to the radiographic stand 22 (a central position in FIG. 2), the image of the breast N is captured with a radiation dose which has been determined on the basis of the thickness of the breast N detected by the radiography device 10. In general, when the thickness of the breast N is large, the amount of radiation which reaches the radiation detector 42 (passes through the breast N) is reduced. Therefore, in this embodiment, a correspondence relationship among the first incident angle, the thickness of the breast N, and a radiation dose is stored in the memory of the radiography device control unit 46 in advance. In this embodiment, the radiation detector 42 outputs high-resolution image information, without performing the binning process. However, the radiation detector 42 may perform the binning process. Then, the image processing unit 45 performs necessary processes, such as a gain correction process, an offset correction process, and a defective pixel correction process, for the image information of the breast N obtained by the radiation detector 42 to generate a radiographic image of the breast N (for example, a RAW format is applied as the format of the image). In addition, for example, the conditions of the subsequent tomosynthesis imaging are determined on the basis of the result of the first imaging process.

In Step 104, the part-of-interest detection unit 47 of the radiography device control unit 46 analyzes the radiographic image generated by the image processing unit 45. The part-of-interest detection unit 47 detects a mutation site that is suspected as a lesion. Then, the process proceeds to Step 106.

In Step 106, the radiography device control unit 46 (part-of-interest detection unit 47) determines whether a mutation site suspected as a lesion has been detected. In the determination, the radiography device control unit 46 (the part-of-interest detection unit 47, particularly, the size detection unit) determines whether a mutation site with a size that is equal to or greater than the first size in the predetermined range has been detected. In a case in which the determination result is "No", the process proceeds to Step 108. In a case in which the determination result is "Yes", the process proceeds to Step 109.

In Step 108, the radiography device control unit 46 performs control such that low resolution and a narrow incident angle range are set as the conditions of tomosynthesis imaging. Specifically, the radiography device control unit 46 performs control such that the radiation detector 42 performs the binning process and the incident angle range during the acquisition of the projection image of the breast is set to a narrow incident angle range. As such, since an image is captured at low resolution, for example, the time required for image processing is shorter than that when an image is captured at high resolution. In addition, since the incident angle range is set to a narrow incident angle range during tomosynthesis imaging, an imaging time is shorter than that when an image is captured in a wide incident angle range. Therefore, in a case in which no mutation site has been detected, it is possible to reduce a burden on the subject W caused by the compression of the breast N during imaging. After the tomosynthesis imaging conditions are set, the process proceeds to Step 120.

In Step 109, the radiography device control unit 46 performs control such that high resolution and a wide incident angle range are set as the conditions of tomosynthesis imaging. That is, the radiography device control unit 46 performs control such that the radiation detector 42 does not perform the binning process and the incident angle range during the acquisition of the projection image of the breast is set to a wide incident angle range. As such, in a case in which only a mutation site has been detected (this includes a case in which both a mutation site that is suspected as a calcification and a mutation site that is suspected as a tumor mass have been detected), tomosynthesis imaging is performed under the conditions of high resolution and a wide incident angle range to obtain a necessary projection image and a necessary tomographic image.

In Step 120, tomosynthesis imaging is performed under the set tomosynthesis imaging conditions. That is, the supporting portion 29 is moved to the maximum angle in the set incident angle range and tomosynthesis imaging starts. For example, imaging is performed while the supporting portion 29 is moved at an angular interval of 1°. In this way, a plurality of projection images corresponding to the set incident angle range are captured. The capture of a radiographic image at each position will be described in detail below. The image processing unit 45 performs necessary processes, such as a gain correction process, an offset correction process, and a defective pixel correction process, for the image information obtained by the radiation detector 42, in which whether to perform the binning process is set, to generate a radiographic image (projection image) with, for example, a RAW format. After tomosynthesis imaging is completed, the fixation of the breast by the compression plate 26 is released. For example, the compression plate 26 is moved in a direction in which it becomes further away from the imaging surface 20 to release the fixation of the breast. Then, the process proceeds to Step 122.

In Step 122, the captured radiographic image is output to the image processing device 50 and the process of the radiography device control unit 46 during imaging ends. Then, in the image processing device 50, the tomographic image generation unit 68 performs image processing, such as FBP, on the basis of the projection image output from the radiography device control unit 46 to generate a tomographic image. The radiography device 10 according to this embodiment is an intelligent device that can perform the detection of a mutation site from a captured two-dimensional image, the setting of tomosynthesis imaging conditions, and tomosynthesis imaging, using only one process of compressing the breast N.

As such, in the process according to this example, similarly, a mutation site is detected from the radiographic image (that is, the two-dimensional image of the breast obtained by the first imaging process) captured before tomosynthesis imaging, imaging conditions are determined on the basis of the detection result, and tomosynthesis imaging is performed. Therefore, it is possible to obtain an accurate tomographic image while reducing a burden on the subject.

In this embodiment, the processes according to the first to third examples have been independently described. However, the user may set the processes to be performed and the processes may be switched according to the setting of the user.

In this embodiment, the resolution of the radiation detector 42 can switch between two types and the incident angle range during tomosynthesis imaging can switch between two types. However, the invention is not limited thereto. For example, each of the resolution and the incident angle range may switch between three or more types. In the case of a structure in which each of the resolution and the incident angle range can switch between three or more types, it is possible to more finely set the tomosynthesis imaging conditions. In addition, in this embodiment, a case in which the radiation detector 42 uses the binning process has been described as an example in which the radiographic image generation unit generates a low-resolution or high-resolution radiographic image. However, the invention is not limited thereto. For example, the above-mentioned thinning-out process of the radiation detector 42 may be used to generate a low-resolution/high-resolution radiographic image.

The radiation in this embodiment is not particularly limited. For example, X-rays or γ-rays may be applied.

For example, the structure and operation of the radiation detector 42 described in this embodiment are illustrative and can be changed according to circumstances, without departing from the scope and spirit of the invention.

What is claimed is:

1. A radiography device that can perform tomosynthesis imaging, comprising:
   a radiation emitting unit that irradiates a subject with radiation at a plurality of different incident angles;
   a radiographic image generation unit that receives the radiation which has been emitted from the radiation emitting unit and passed through the subject and can generate radiographic images of the subject with different resolutions;
   a part-of-interest detection unit that detects a mutation site suspected as a lesion from a radiographic image of the subject which is generated by the radiographic image generation unit with the radiation emitted from the radiation emitting unit to the subject at a predetermined incident angle before the tomosynthesis imaging; and
   a radiography device control unit that performs control such that a first tomosynthesis imaging process in which the tomosynthesis imaging is performed in a first incident angle range and the radiographic image generation unit generates a plurality of projection images of the subject at a first resolution is performed in a case in which the part-of-interest detection unit does not detect the mutation site and a second tomosynthesis imaging process is performed at least in a second incident angle range wider than the first incident angle range or at a second resolution higher than the first resolution in a case in which the part-of-interest detection unit detects the mutation site.

2. The radiography device according to claim 1,
   wherein, in a case in which the part-of-interest detection unit detects only the mutation site with a first size in a predetermined range, the radiography device control unit performs control such that the second tomosynthesis imaging process is performed at the second resolution and in the first incident angle range.

3. The radiography device according to claim 1,
   wherein, in a case in which the part-of-interest detection unit detects both the mutation site with a first size in a predetermined range and the mutation site with a size greater than the first size, the radiography device control unit performs control such that the second tomosynthesis imaging process is performed at the second resolution and in the second incident angle range.

4. The radiography device according to claim 1,
wherein, in a case in which the part-of-interest detection unit detects only the mutation site with a size greater than a first size in a predetermined range, the radiography device control unit performs control such that the second tomosynthesis imaging process is performed at the first resolution and in the second incident angle range.

5. The radiography device according to claim 1,
wherein, in a case in which the part-of-interest detection unit detects only the mutation site with a size greater than a first size in a predetermined range, the radiography device control unit performs control such that the second tomosynthesis imaging process is performed at the second resolution and in the second incident angle range.

6. The radiography device according to claim 3,
wherein the mutation site with a size greater than the first size is a mutation site suspected as a tumor mass.

7. The radiography device according to claim 2,
wherein the mutation site with the first size is a mutation site suspected as a calcification.

8. A radiography method that is performed in a radiography device which can perform tomosynthesis imaging and includes a radiation emitting unit that irradiates a subject with radiation at a plurality of different incident angles and a radiographic image generation unit that receives the radiation which has been emitted from the radiation emitting unit and passed through the subject and can generate radiographic images of the subject with different resolutions, the method comprising:
allowing the radiation emitting unit to irradiate the subject with the radiation at a predetermined incident angle, allowing the radiographic image generation unit to generate a radiographic image of the subject, and detecting a mutation site suspected as a lesion from the radiographic image, before the tomosynthesis imaging;
performing a first tomosynthesis imaging process in which the tomosynthesis imaging is performed in a first incident angle range and the radiographic image generation unit generates a plurality of projection images of the subject at a first resolution in a case in which the mutation site is not detected; and
performing a second tomosynthesis imaging process at least in a second incident angle range wider than the first incident angle range or at a second resolution higher than the first resolution in a case in which the mutation site is detected.

9. The radiography method according to claim 8,
wherein, in the tomosynthesis imaging, in a case in which only the mutation site with a first size in a predetermined range is detected, the second tomosynthesis imaging process is performed at the second resolution and in the first incident angle range.

10. The radiography method according to claim 8,
wherein, in the tomosynthesis imaging, in a case in which both the mutation site with a first size in a predetermined range and the mutation site with a size greater than the first size are detected, the second tomosynthesis imaging process is performed at the second resolution and in the second incident angle range.

11. The radiography method according to claim 8,
wherein, in the tomosynthesis imaging, in a case in which only the mutation site with a size greater than a first size in a predetermined range is detected, the second tomosynthesis imaging process is performed at the first resolution and in the second incident angle range.

12. The radiography method according to claim 8,
wherein, in the tomosynthesis imaging, in a case in which only the mutation site with a size greater than a first size in a predetermined range is detected, the second tomosynthesis imaging process is performed at the second resolution and in the second incident angle range.

13. The radiography method according to claim 9,
wherein the mutation site with a size greater than the first size is a mutation site suspected as a tumor mass.

14. The radiography method according to claim 9,
wherein the mutation site with the first size is a mutation site suspected as a calcification.

15. A non-transitory storage medium storing a program that causes a computer to execute radiography processing, the radiography processing comprising:
irradiating, by a radiation emitting unit of a radiography device, a subject with radiation at a predetermined incident angle;
generating, by a radiographic image generation unit of the radiography device, a radiographic image of the subject, and detecting a mutation site suspected as a lesion from the radiographic image;
performing a first tomosynthesis imaging process in which a tomosynthesis imaging is performed in a first incident angle range and the radiographic image generation unit generates a plurality of projection images of the subject at a first resolution in a case in which the mutation site is not detected; and
performing a second tomosynthesis imaging process at least in a second incident angle range wider than the first incident angle range or at a second resolution higher than the first resolution in a case in which the mutation site is detected.

* * * * *